US005582983A

United States Patent [19]

Anderson et al.

[11] Patent Number: 5,582,983

[45] Date of Patent: Dec. 10, 1996

[54] GENETIC MARKERS AND METHODS OF IDENTIFYING ALEXANDRIUM (DINOPHYCEAE) SPECIES

[75] Inventors: Donald M. Anderson, Marion; Christopher A. Scholin, E. Falmouth, both of Mass.

[73] Assignee: Woods Hole Oceanographic Institution, Woods Hole, Mass.

[21] Appl. No.: 259,745

[22] Filed: Jun. 14, 1994

Related U.S. Application Data

[63] Continuation of Ser. No. 967,637, Oct. 28, 1992, abandoned.

[51] Int. Cl.$^6$ .............................. C12Q 1/68; C12P 19/34; C07H 21/04

[52] U.S. Cl. .......................... 435/6; 430/91.2; 536/24.32; 536/24.33; 935/77; 935/78

[58] Field of Search .................. 435/6, 91.2; 536/24.32, 536/24.33; 935/77, 78

[56] References Cited

U.S. PATENT DOCUMENTS 5,034,315 7/1991 Jensen et al. .............................. 435/6

FOREIGN PATENT DOCUMENTS 8803957 6/1988 WIPO .

OTHER PUBLICATIONS

Amann et al., "Combination of 16S rRNA–Targeted Oligonucleotide Probes with Flow Cytometry for Analyzing Mixed Microbial Populations", Applied and Environmental Microbiology, Jun. 1990, pp. 1919–1925.

DeLong et al., "Fluorescent Ribosomal RNA Probes For Clinical Applications: A Research Review", Diagnostics & Clinical Testing, vol. 28, May 1990, pp. 41–44.

DeLong et al., "Phylogenetic Stains: Ribosomal RNA –Based Probes for the Identification of Single Cells", Science, 10 Mar. 1989, vol. 243, pp. 1360–1363.

Destombe et al., "Nucleotide sequence of the 18S ribosomal RNA genes from the marine dinoflagellate *Alexandrium tamarense* (Gonyaulacales, Dinophyta)", Phycologia, vol. 31(1), 1992, pp. 121–125.

Distel et al., "Phylogenetic Characterization and In Situ Localization of the Bacterial Symbiont of Shipworms (Teredinidae: Bivalvia) by using 16S rRNA Sequence Analysis and Oligodeoxynucleotide Probe Hybridization", Applied and Environmental Microbiology, vol. 57 No. 8, Aug. 1991, pp. 2376–2382.

Giovannoni et al., "Phylogenetic Group–Specific Oligodeoxynucleotide Probes for Identification of Single Microbial Cells", Journal of Bacteriology, vol. 170, Feb. 1988, pp. 720–726.

Gutell et al., "A compilation of large subunit (23S–like) ribosomal RNA sequences presented in a secondary structure format", Nucleic Acids Research, vol. 18 Supplement, pp. 2319–2330.

Hill et al., "Gene Probes Used in Food Microbiology", Biotechnology, pp. 139–165.

Neefs et al., "Compilation of small ribosomal subunit RNA Sequences", Nucleic Acids Research, vol. 18, Supplement, pp. 2237–2248, 1990.

Destombe et al Phycologica (1992) 31:121–125.

Len aers et al, J Molec Evol (1991) 32:53–63.

Anderson, Toxic Marine Phytoplankton, 1990, Elsevier Science Publishing Co, Inc., Granele et al Ed, pp. 41–51.

*Primary Examiner*—W. Gary Jones
*Assistant Examiner*—Carla Myers
*Attorney, Agent, or Firm*—George W. Neuner

[57] ABSTRACT

Nucleotide sequences from various species of Alexandrium are described. The sequences are used to construct nucleotide probes for assaying samples to determine the presence of selected species of Alexandrium.

8 Claims, 16 Drawing Sheets

| SEQUENCE ID. NO. | STRAIN | 1 | 50 |
|---|---|---|---|
| 11 | PW06 | TAAGTAAGTGGTGGAAATTAAACCA | AATAGGATATCTTTAGTAATTGCGA |
| 12 | PI32 | ......................... | ......................... |
| 13 | BGt1 | ......................... | ......................... |
| 14 | AFNFA3.1 | ......................... | ...G..................... |
| 15 | GtCA29 | ......................... | ...G..................... |
| 16 | AFNFA3.2 | ......................... | ...G..................... |
| 17 | AFNFA4 | ......................... | ...G..................... |
| 18 | GTMPSHER | ......................... | ...G..................... |
| 19 | I72/24#1 | ......................... | ...G..................... |
| 20 | OF041 | ......................... | ...G..................... |
| 21 | OF051 | ......................... | ...G..................... |
| 22 | PGT183 | ......................... | ...G....T................ |
| 23 | PE1V | ......................... | ...G....T................ |
| 24 | PE2V | ......................... | ...G....T................ |
| 25 | WKS1 | ......................... | ...G....T................ |
| 26 | OF101 | ......................... | .C.G....C....C..........C |
| 27 | TN9 | ......................... | .C.G....C....C..........C |
| 28 | WKS8 | ......................... | .C.G....C....C..........C |
| 29 | ATJP03 | ......................... | .C.G....C....C..Y.......C |
| 30 | ACJP03 | ......................... | .C.G....C....C..........C |
| 31 | ACPP01 | ......................... | .C.G....C....C..........C |
| 32 | ACPP02 | ......................... | .C.G....C....C..........C |
| 33 | G.CRUX | ......................... | .C.G....C....C..........C |
| 34 | GHOPE1 | ......................... | .C.G....C...............C |
| 35 | GHOPE2 | ......................... | .C.G....C...............C |
| 36 | ATBBO1 | ......................... | .C.G....C...............C |
| 37 | CU13 | ......................... | ...G....TC............... |
| 38 | CU1 | ......................... | ...G....TC...A........... |
| 39 | AABBO1/2 | ......................... | ...G....TC...A........... |
| 40 | PA5V | ......................... | ...G....TC...A........... |
| 41 | AMAD01 | ......G.C........A.G..... | ...G....TC...A........... |
| 42 | AMAD06 | ......G.C........A.G..... | ...G....TC...A........... |
| 43 | GTPORT | ......G.C........A.G..... | ...G....TC...A........... |
| 44 | TC02 | ......G.C........A....... | ...G....TC...A......G.... |
| 45 | P micans | ........C..A...U.AG....U. | ........UC.C.C......G.... |

FIG. 1(a)

```
SEQUENCE
ID. NO.                               begin D1 Domain
        STRAIN     51                        ->                      100
  11    PW06       ATGAACAAGGATATGCTTAGCTTGA CAAMTGGAGCTATTGGCTTTGAATT
  12    PI32       ......................... ...A.....................
  13    BGt1       ......................... ....Y....................
  14    AFNFA3.1   ......................... ...A.....................
  15    GtCA29     ......................... ...A.....................
  16    AFNFA3.2   ......................... ...A.....................
  17    AFNFA4     ......................... ..MA.....................
  18    GTMPSHER   ......................... ...A.....................
  19    I72/24#1   ......................... ...A.....................
  20    OF041      ......................... ...A.K...................
  21    OF051      ......................... ...A.....................
  22    PGT183     ......................... ...A.......T..........G..
  23    PE1V       ......................... ...A.......T..........G..
  24    PE2V       ......................... ...A.......T..........G..
  25    WKS1       ......................... ...A.......T..........G..
  26    OF101      ......C.................. ...A.......GC.....C......
  27    TN9        ......C.................. ...A.......GC.....C......
  28    WKS8       ......C.................. ...A.......GC.....C......
  29    ATJP03     ......C.................. ...A.......GC.....C......
  30    ACJP03     ......C.................. ...A.......GC.....C......
  31    ACPP01     ......C.................. ...A.......GC.....C......
  32    ACPP02     ......C.................. ...A.......GC.....C......
  33    G.CRUX     ......C.................. ...A.......GC.....C......
  34    GHOPE1     ......C.................. ...A.......GC.....C......
  35    GHOPE2     ......C.................. ...A.......GC.....C......
  36    ATBB01     ......C.................. ...A.......GC............
  37    CU13       ......................... U..T...G...TC..........Y.
  38    CU1        ...........C............. ...T......CTC......C..C..
  39    AABB01/2   ...........C............. ...T......CTC......C..C..
  40    PA5V       ...........C............. ...T......CTC......C..C..
  41    AMAD01     ...........A.....C....... A..A...G..CT.............
  42    AMAD06     ...........A.....C....... A..A...G..CT.............
  43    GTPORT     ...........A.....C....... A..A...G..CT.............
  44    TC02       ...........AC....C.A..... A..TC..G...TC....C.......
  45    P micans   .......G....CA...C...A..C A..U...G-.CC.C...C.......
```

FIG. 1(b)

| SEQUENCE ID. NO. | STRAIN | 101 | 150 |
|---|---|---|---|
| 11 | PW06 | GTATTGTGGAAATGTATTACCAACA | GAGGTGCAGGTGCCAGCCTATTGAA |
| 12 | PI32 | ......................... | ......................... |
| 13 | BGt1 | ......................... | ......................... |
| 14 | AFNFA3.1 | ......................... | .................M....... |
| 15 | GtCA29 | ......................... | ......................... |
| 16 | AFNFA3.2 | .....TGT.G............... | .................M....... |
| 17 | AFNFA4 | .... TGT.G............... | ......................... |
| 18 | GTMPSHER | ......................... | .................M....... |
| 19 | I72/24#1 | ......................... | ......................... |
| 20 | OF041 | ..............Y.......... | ......................... |
| 21 | OF051 | ...........R..Y.......... | ......................... |
| 22 | PGT183 | ................CC....... | ........A...Y.....AT..... |
| 23 | PE1V | ................CC....... | ........A...T.....AT..... |
| 24 | PE2V | ................CC....... | ........A...T.....AT..... |
| 25 | WKS1 | ................CC....... | ........A...T.....AT..... |
| 26 | OF101 | .........G............... | ............T.....AT..... |
| 27 | TN9 | .........G............... | ............T.....AT..... |
| 28 | WKS8 | .........G............... | ............T.....AT..... |
| 29 | ATJP03 | .........G............... | ............T.....AT..... |
| 30 | ACJP03 | .........G............... | ............T.....AT..... |
| 31 | ACPP01 | .........G............... | ............T.....AT..... |
| 32 | ACPP02 | .........G............... | ............T.....AT..... |
| 33 | G.CRUX | .........G............... | ............T.....AT..... |
| 34 | GHOPE1 | .........G............... | ............T.....AT..... |
| 35 | GHOPE2 | .........G............... | ............T.....AT..... |
| 36 | ATBBO1 | ............Y............ | ..................AT..... |
| 37 | CU13 | ..G..T.T................. | ............TT...A.....G. |
| 38 | CU1 | .....T.T................. | ............T............ |
| 39 | AABB01/2 | .....T.T................. | ............T............ |
| 40 | PA5V | .....T.T................. | ............T............ |
| 41 | AMAD01 | ...A.T.T..........G....TG | ....C........A........... |
| 42 | AMAD06 | ...A.T.T..........G....TG | ....C........A........... |
| 43 | GTPORT | ...A.T.T..........G....TG | ....C........A........... |
| 44 | TC02 | ...A.T.T..........G....TG | ....C........A....A...... |
| 45 | P micans | ...G.C.C..G...C..CG....UG | ....C....A..UA.....C...G. |

FIG. 1(c)

| SEQUENCE ID. NO. | STRAIN | 151 | 200 |
|---|---|---|---|
| 11 | PW06 | ATAAAGCGTCAATGAGGGTGAGAAT | CCTGTTTGTCATGTGCARCCCTTTG |
| 12 | PI32 | ......................... | .................G....... |
| 13 | BGt1 | ......................... | .................G....... |
| 14 | AFNFA3.1 | ...R..................... | ........Y........G....... |
| 15 | GtCA29 | ......................... | .................G....... |
| 16 | AFNFA3.2 | ...R..................... | ........Y........G....... |
| 17 | AFNFA4 | ......................... | .................G....... |
| 18 | GTMPSHER | R........................ | ........Y........G....... |
| 19 | I72/24#1 | ......................... | ........Y........G....... |
| 20 | OF041 | ......................... | .................G....... |
| 21 | OF051 | ......................... | .................G....... |
| 22 | PGT183 | .G....................... | .................G....C.. |
| 23 | PE1V | .G......Y................ | .................G....C.. |
| 24 | PE2V | .G....................... | .................G....C.. |
| 25 | WKS1 | .G....................... | .................G....C.. |
| 26 | OF101 | .G.....A...............G. | .................G..T.C.. |
| 27 | TN9 | .G.....A...............G. | ....Y............G..T.C.. |
| 28 | WKS8 | .G.....A...............G. | .................G..T.C.. |
| 29 | ATJP03 | .G.....A...............G. | .................G..T.C.. |
| 30 | ACJP03 | .G.....A...............G. | .................G..T.C.. |
| 31 | ACPP01 | .G.....A...............G. | .................G..T.C.. |
| 32 | ACPP02 | .G.....A...............G. | .................G..T.C.. |
| 33 | G.CRUX | .G.....A...............G. | .................G..T.C.. |
| 34 | GHOPE1 | .G.....A...............G. | .................G..T.C.. |
| 35 | GHOPE2 | .G.....A...............G. | .................G..T.C.. |
| 36 | ATBBO1 | .G....................... | ............A....G....C.. |
| 37 | CU13 | .G....................... | ...T.............GT...C.. |
| 38 | CU1 | .G....................... | .................AT...C.. |
| 39 | AABB01/2 | .G....................... | .................AT...C.. |
| 40 | PA5V | .G....................... | .................AT...C.R |
| 41 | AMAD01 | .G.....................T. | ...T........T....GT...CC. |
| 42 | AMAD06 | .G.....................T. | ...T........T....GT...CC. |
| 43 | GTPORT | .G.....................T. | ...T........T....GT...CC. |
| 44 | TC02 | .G..........A..A.....A... | ...T........T....G....CC. |
| 45 | P micans | .A.G...A....C..........G. | ..C.........C....RU..CCCA |

FIG. 1(d)

| SEQUENCE ID. NO. | STRAIN | 201 end D1 domain <- 250 |
|---|---|---|
| 11 | PW06 | TGCACGGTGTATATTTGCTGAGTCA CACTCCTTGGCATTGGAATGCAAAG |
| 12 | PI32 | ......................... ......................... |
| 13 | BGt1 | ......................... ......................... |
| 14 | AFNFA3.1 | ......................... ......................... |
| 15 | GtCA29 | ......................... ......................... |
| 16 | AFNFA3.2 | ......................... ......................... |
| 17 | AFNFA4 | ......................... ......................... |
| 18 | GTMPSHER | ......................... ......................... |
| 19 | I72/24#1 | ......................... ......................... |
| 20 | OF041 | ......................... ................M........ |
| 21 | OF051 | ......................... ................M........ |
| 22 | PGT183 | ......................... ......................... |
| 23 | PE1V | ......................... ......................... |
| 24 | PE2V | ......................... ......................... |
| 25 | WKS1 | ......................... ......................... |
| 26 | OF101 | ......................... .......Y................. |
| 27 | TN9 | ......................... .......Y................. |
| 28 | WKS8 | ......................... ......................... |
| 29 | ATJP03 | ......................... ......................... |
| 30 | ACJP03 | ......................... ......................... |
| 31 | ACPP01 | ......................... .......Y................. |
| 32 | ACPP02 | ......................... .......Y................. |
| 33 | G.CRUX | ......................... .......Y................. |
| 34 | GHOPE1 | ......................... ......................... |
| 35 | GHOPE2 | ......................... ......................... |
| 36 | ATBB01 | ......................... ......................... |
| 37 | CU13 | ............G............ ......................... |
| 38 | CU1 | ............G............ ......................... |
| 39 | AABB01/2 | ............G............ ......................... |
| 40 | PA5V | ............G............ ......................... |
| 41 | AMAD01 | ........A........AC...... .......C................. |
| 42 | AMAD06 | ........A........AC...... .......C................. |
| 43 | GTPORT | ........A........AC...... .......C................. |
| 44 | TC02 | ........A........AC...... .......C................. |
| 45 | P micans | .......C..GCU.C.AA-.....G .GU....C..A......GC.UC..U |

FIG. 1(e)

| SEQUENCE ID. NO. | STRAIN | 251 — 300 |
|---|---|---|
| 11 | PW06 | TGGGTGGTAAGTTTCATGTAAAGGT AAACATGCAAYTGAGACTGATAGCA |
| 12 | PI32 | ......................... ......................... |
| 13 | BGt1 | .....R................... ......................... |
| 14 | AFNFA3.1 | ...................M..... ......................... |
| 15 | GtCA29 | ......................... ......................... |
| 16 | AFNFA3.2 | ...................M..... ......................... |
| 17 | AFNFA4 | ...................M..... ..........T.............. |
| 18 | GTMPSHER | ...................M..... ......................... |
| 19 | I72/24#1 | ...................M..... ..........T.............. |
| 20 | OF041 | ......................... ......................... |
| 21 | OF051 | ......................... ......................... |
| 22 | PGT183 | .................AC...... ...T......T.............. |
| 23 | PE1V | .................AC...... ...T......T.............. |
| 24 | PE2V | .................AC...... ...T......T.............. |
| 25 | WKS1 | .................AC...... ...T......T.............. |
| 26 | OF101 | ..................C...... ...T......T.............G |
| 27 | TN9 | ..................C...... ...T......T.............R |
| 28 | WKS8 | ..................C...... ...T......T.............G |
| 29 | ATJP03 | ..................C...... ...T......T.............G |
| 30 | ACJP03 | ..................C...... ...T......T.............G |
| 31 | ACPP01 | ..................C...... ..MT......T.............G |
| 32 | ACPP02 | ..................C...... ...T......T.............G |
| 33 | G.CRUX | ..................C...... ...T......T.............G |
| 34 | GHOPE1 | ..................C...... ...T......T.............G |
| 35 | GHOPE2 | ..................C...... ...T......T.............G |
| 36 | ATBBO1 | ..................C...... ...T......T.............G |
| 37 | CU13 | ......................... ...T..AUG.T............TG |
| 38 | CU1 | ......................... ...T..AGG.T.............. |
| 39 | AABB01/2 | ......................... ...T..AGG.T.............. |
| 40 | PA5V | ......................... ...T..AGG.T.............. |
| 41 | AMAD01 | ..........A..C........... ...T..ATT.T.............. |
| 42 | AMAD06 | ..........A..C........... ...T..ATT.T.............. |
| 43 | GTPORT | ..........A..C........... ...T..ATT.T.............. |
| 44 | TC02 | ..........A............A. T..T..ATT.T....R........G |
| 45 | P micans | .......C..GCU.C.AA-.....G .GU....C..A......GC.UC..U |

FIG. 1(f)

| SEQUENCE ID. NO. | STRAIN | 301 | begin D2 domain 350-> |
|---|---|---|---|
| 11 | PW06 | CACAAGURCCATGAGGGAAATATGA | AAAGGACTTTGAAAAGAGAATTAAA |
| 12 | PI32 | ......................... | ......................... |
| 13 | BGt1 | ......................... | ......................... |
| 14 | AFNFA3.1 | ......................... | ......................... |
| 15 | GtCA29 | ......................... | ......................... |
| 16 | AFNFA3.2 | ......................... | ......................... |
| 17 | AFNFA4 | ......................... | ......................... |
| 18 | GTMPSHER | ......................... | ......................... |
| 19 | I72/24#1 | .......A................. | ......................... |
| 20 | OF041 | ......................... | .............C.T...G....C |
| 21 | OF051 | ......................... | .............C.T...G....C |
| 22 | PGT183 | .......A................. | ......................... |
| 23 | PE1V | .......A................. | ......................... |
| 24 | PE2V | .......A................. | ......................... |
| 25 | WKS1 | .......A................. | ......................... |
| 26 | OF101 | .......A..........C...... | .............C........... |
| 27 | TN9 | .......A..........C...... | .............C........... |
| 28 | WKS8 | .......A..........C...... | .............C........... |
| 29 | ATJP03 | .......A..........C...... | .............C........... |
| 30 | ACJP03 | .......A..........C...... | .............C........... |
| 31 | ACPP01 | .......A..........C...... | .............C........... |
| 32 | ACPP02 | .......A..........C...... | .............C........... |
| 33 | G.CRUX | .......A..........C...... | .............C........... |
| 34 | GHOPE1 | .......A..........C...... | .............M........... |
| 35 | GHOPE2 | .......A..........C...... | .............C........... |
| 36 | ATBB01 | .......A..........C...... | ......................... |
| 37 | CU13 | .......A................. | ......................... |
| 38 | CU1 | ......................... | ......................... |
| 39 | AABB01/2 | .......A................. | ......................... |
| 40 | PA5V | .......A................. | ......................... |
| 41 | AMAD01 | A......A................. | ......................... |
| 42 | AMAD06 | A......A................. | ......................... |
| 43 | GTPORT | A......A................. | ......................... |
| 44 | TC02 | A......A................. | ......................... |
| 45 | P micans | A......A............GG... | ...................G..... |

FIG. 1(g)

| SEQUENCE ID. NO. | STRAIN | 351 400 |
|---|---|---|
| 11 | PW06 | TGAGTTTGTATTTGCTGAACACAAA GTAAACAGACTTGATTTGCTTGG-T |
| 12 | PI32 | ......................... .......................-. |
| 13 | BGt1 | ......................... .......................-. |
| 14 | AFNFA3.1 | ......................... .......................-. |
| 15 | GtCA29 | ......................... .......................-. |
| 16 | AFNFA3.2 | ......................... .......................-. |
| 17 | AFNFA4 | ......................... .......................-. |
| 18 | GTMPSHER | ......................... .......................-. |
| 19 | I72/24#1 | ......................... .......................-. |
| 20 | OF041 | ...C..................... .......................-. |
| 21 | OF051 | ...C..................... .......................-. |
| 22 | PGT183 | ......................... .C.....................-. |
| 23 | PE1V | ......................... .C...................R.-. |
| 24 | PE2V | ......................... .C.....................-. |
| 25 | WKS1 | ......................... .C.....................-. |
| 26 | OF101 | ................A........ .................C..CA.-. |
| 27 | TN9 | ................A........ .................C..CA.-. |
| 28 | WKS8 | ................A........ .................C..CA.-. |
| 29 | ATJP03 | ................A........ .................C..CAR-. |
| 30 | ACJP03 | ................A........ .................C..CA.-. |
| 31 | ACPP01 | ................A........ .................C..CA.-. |
| 32 | ACPP02 | ................A........ .................C..CA.-. |
| 33 | G.CRUX | ......Y.........A........ .................C..CA.-. |
| 34 | GHOPE1 | ................A........ .................C..CA.-. |
| 35 | GHOPE2 | ................A........ .................C..CA.-. |
| 36 | ATBB01 | C........................ .........TG......C...A.-. |
| 37 | CU13 | .....................G... .........T.......TGC...G. |
| 38 | CU1 | .....................G... A........T.....G.TGC.T.G. |
| 39 | AABB01/2 | .....................G... A........T.....G.TGC.T.G. |
| 40 | PA5V | .....................G... A........T.....G.TGC.T.G. |
| 41 | AMAD01 | A....C..C............G... .C.......A.......TAC.T.G. |
| 42 | AMAD06 | A....C..C............G... .C.......A.......TAC.T.G. |
| 43 | GTPORT | A....C..C............G... .C.......A.......TAC.T.G. |
| 44 | TC02 | A....C..C.C..........G... .C.......AG.....ATGC.T.G. |
| 45 | P micans | A.UGCC..A.A........AGGG.. .CG..UG..ACCAG.G.UGC.U.GC |

FIG. 1(h)

| SEQUENCE ID. NO. | STRAIN | 401 | 451 |
|---|---|---|---|
| 11 | PW06 | GGGAGTGTTGCACTTGCTT-GACAA | GAGCTTTGGGC-TGTGGGTGTAATG |
| 12 | PI32 | ...................-..... | ...........-.....R....... |
| 13 | BGt1 | ...................-..... | ...........-............. |
| 14 | AFNFA3.1 | ...................-..... | ...........-............. |
| 15 | GtCA29 | ...................-..... | ...........-............. |
| 16 | AFNFA3.2 | ...................-..... | ...........-............. |
| 17 | AFNFA4 | ...................-..... | ...........-............. |
| 18 | GTMPSHER | ...................-..... | ...........-............. |
| 19 | I72/24#1 | ........W..........-..... | ...........-............. |
| 20 | OF041 | ...................-..... | ...........-............. |
| 21 | OF051 | ...................-..... | ...........-............. |
| 22 | PGT183 | .A..T...A.TG.......-..... | T..G...T...-........A.... |
| 23 | PE1V | .A..T...A.TG.......-..... | T..G...T...-........A.... |
| 24 | PE2V | .A..T...A.TG.......-..... | T..G...T...-........A.... |
| 25 | WKS1 | .A..T...A.TG.......-..... | T..G...T...-........A.... |
| 26 | OF101 | .A..T...A.TGM......-R.... | TG.G...T...-..CAA...C...A |
| 27 | TN9 | .A..T...A.TG.......-R.... | TG.G...T...-..CAA...C...A |
| 28 | WKS8 | .A..T...A.TGM......-R.... | TG.G...K...-..CAA...C...A |
| 29 | ATJP03 | .A..T...A.TG.......-R.... | TG.G...T...-..CAA...C...A |
| 30 | ACJP03 | .A..T...A.TG.......-A.... | TG.G...T...-..CAA...C...A |
| 31 | ACPP01 | .A..T...A.TG.......-R.... | TG.G...T...-..CAA...C...A |
| 32 | ACPP02 | .A..T...A.TGM......-R.... | TG.G...T...-..CAA...C...A |
| 33 | G.CRUX | .A..T...A.TG.......-R.... | TG.G...T...-..CAA...C...A |
| 34 | GHOPE1 | .A..T...A.TGM......-R.... | TG.G.W.T...-..CAA...C...A |
| 35 | GHOPE2 | .A..T...A.TG.......-R.... | TG.G...T...-..CAA...C...A |
| 36 | ATBBO1 | .A..T...A..........-..... | T..G...T...-G.......C.... |
| 37 | CU13 | .A..T...G.TG.......-....- | CTTA.G.-..T-...AA..AC.... |
| 38 | CU1 | .A..T...G.TG.......-..... | T..G...T.AT-........CG... |
| 39 | AABB01/2 | .A..T...G.TG.......-..... | T..G...T.AT-........CG... |
| 40 | PA5V | .A..T...G.TG.......-..... | T..G...T.AT-........CG... |
| 41 | AMAD01 | .A..T.....TG...A..CTAT..T | TTATA.G.TTGA........CG... |
| 42 | AMAD06 | .A..T.....CG...A..CTAT..T | TTATA.G.TTGA........CG... |
| 43 | GTPORT | .A..T.....CG...A..CTAT..T | TTATA.G.TTGA........CG... |
| 44 | TC02 | AA..T......GTC.TG..GTT.TG | C.A...G..CGCA....T.C.T.CC |
| 45 | P micans | .A....UG.CGUACGCAC.UCG.GU | .U.G.GGUUCUUGCCUU.U.UGUCA |

FIG. 1(i)

```
SEQUENCE
ID. NO.   STRAIN      452                                                500
  11      PW06        ATTCTTTCTTTGCATGCCAGTTTCT ATTTGTACATCTGATTACCTTTGCA
  12      PI32        ......................... .........................
  13      BGt1        ......................... .........................
  14      AFNFA3.1    ......................... ..G......................
  15      GtCA29      ......................... ..G......................
  16      AFNFA3.2    ......................... .........................
  17      AFNFA4      ......................... .........................
  18      GTMPSHER    ......................... .........................
  19      I72/24#1    ...M..W.................. .........................
  20      OF041       ......................... .........................
  21      OF051       ......................... .........................
  22      PGT183      ....................G.... ..G......T...............
  23      PE1V        ....................G.... ..G......T...............
  24      PE2V        ....................G.Y.. ..G......T...............
  25      WKS1        ....................G.... ..G......T...............
  26      OF101       ......G....TG..........T. ..G..G...T...............
  27      TN9         ......G....TG..........T. ..G..G...T...............
  28      WKS8        ......G....TG..........T. ..G..G...T...............
  29      ATJP03      ......G....TG..........T. ..G..G...T...............
  30      ACJP03      ......G....TG..........T. ..GW.G...T...............
  31      ACPP01      ......G....TG..........T. ..G..G...T...............
  32      ACPP02      ......G....TG..........T. ..G..G...T...............
  33      G.CRUX      ......G....TG..........T. ..G..G...T...............
  34      GHOPE1      ...M..G....TG.R..M.....T. ..G..G...T..R........K...
  35      GHOPE2      ......G....TG....M.....T. ..G..G...T...........K...
  36      ATBB01      ......G....T............. ..G..G...T..........G....
  37      CU13        ......A....TG..........T. -.GC--....T...AC.UUC....G
  38      CU1         ......G.....T............ .........T.........C.....
  39      AABB01/2    ......G.....T............ .........T.........C.....
  40      PA5V        ......G.....T............ .........T.........C.....
  41      AMAD01      G.....A.C...A...T...C.... ....C.G..AA.C......C.....
  42      AMAD06      G.....A.C...A...T...C.... ....C.G..AA.C......C.....
  43      GTPORT      G.....A.C...A...T...C.... ....C.G..AA.C......C.....
  44      TC02        T.GTC.G.CA-.------ .---... -...C.G..AA.C.GA...C.G...
  45      P micans    UGG.UGG.UG..UGUG.U..GUA.A AC.CAU....GGACUGU.UCCU.CG
```

FIG. 1(j)

| SEQUENCE ID. NO. | STRAIN | 501 | 550 |
|---|---|---|---|
| 11 | PW06 | CATGAATGATAAGTCTCCTGTGGGG | GGTGGATTGCATGTGCATGTAATGA |
| 12 | PI32 | ......................... | ......................... |
| 13 | BGt1 | ......................... | ......................... |
| 14 | AFNFA3.1 | ......................... | ......................... |
| 15 | GtCA29 | ......................... | ......................... |
| 16 | AFNFA3.2 | ......................... | ......................... |
| 17 | AFNFA4 | ......................... | ......................... |
| 18 | GTMPSHER | ......................... | ......................... |
| 19 | I72/24#1 | ......................... | ......................... |
| 20 | OF041 | .............Y........... | .R....................... |
| 21 | OF051 | ......................... | .R....................... |
| 22 | PGT183 | ........GY..T.T.....C.... | ......................... |
| 23 | PE1V | ........G...T.T.....C.... | ......................... |
| 24 | PE2V | ...R....G..RTYT.....C.... | ......................... |
| 25 | WKS1 | ........G...T.T.....C.R.. | ......................... |
| 26 | OF101 | ........G...T.T.....C.... | T...........A............ |
| 27 | TN9 | ........GY..T.T.....CC... | T...........A............ |
| 28 | WKS8 | ........G...T.T.....C.... | T...........A............ |
| 29 | ATJP03 | ........G...T.T.....C.... | T...........A............ |
| 30 | ACJP03 | ........G...T.T.....C.... | T.W.........A............ |
| 31 | ACPP01 | ........G...T.T.....C.... | T...........A............ |
| 32 | ACPP02 | ........G...T.T.....C.... | T...........A............ |
| 33 | G.CRUX | ........G...T.T.....C.... | T...........A............ |
| 34 | GHOPE1 | ........G...T.T.....C.... | T...........A......W..... |
| 35 | GHOPE2 | ........G...T.C.....C.... | T...........W............ |
| 36 | ATBB01 | .T......G...T.T.....C.... | ............A..........T. |
| 37 | CU13 | T.......G...TAT.....Y.... | .T..........ACGT......GC. |
| 38 | CU1 | ........G...T.T.....C.... | TT.............TT...G.... |
| 39 | AABB01/2 | ........G...T.T.....C.... | TT.............TT...G.... |
| 40 | PA5V | ........G...T.T.....C.... | TT.............TT...G.... |
| 41 | AMAD01 | ........G...C.TG....C...T | AT....A........TT..C..... |
| 42 | AMAD06 | ........G...Y.TG....C...T | AT....A........TT..C..... |
| 43 | GTPORT | ........G...T.TG....C...T | AT....A........TT..C..... |
| 44 | TC02 | .....C.TG...AA.G....C...T | .T....A........TT..CT.... |
| 45 | P micans | .GCAGCCU.C-..GAU.G..GAAAA | C.CCAGGG.CA..G.AG..UACC.C |

FIG. 1(k)

| SEQUENCE ID. NO. | STRAIN | 551 600 |
|---|---|---|
| 11 | PW06 | TTTGTGT-TTTGATAMATGTGTCTG GTG-TATGTGTGTGTTCC-TGTG |
| 12 | PI32 | .......-................. ...-..............-.... |
| 13 | BGt1 | .......-.............Y... ...-..............-.... |
| 14 | AFNFA3.1 | .......-.......A......... ...-..............-.... |
| 15 | GtCA29 | .K.....-.......A......... ...-.........**..M-.... |
| 16 | AFNFA3.2 | .......-.......A......... ...-.........**...-.... |
| 17 | AFNFA4 | .......-.......A.K....... ...-.........**...-.... |
| 18 | GTMPSHER | .......-.......A......... ...-.........**..M-.... |
| 19 | I72/24#1 | .......-.......A......... ...-.........**...-.... |
| 20 | OF041 | .......-.......AM........ ...-.........**...-.... |
| 21 | OF051 | .......-................. ...-.........**...-.... |
| 22 | PGT183 | .......-......GA......... ...-...C..T.T.....A.... |
| 23 | PE1V | .......-......GA......... ...-...C..T.T.....A.... |
| 24 | PE2V | .......-......GA......... ...-...C..T.T.....A.... |
| 25 | WKS1 | .......-......GA......... ...-...C..T.T.....A.... |
| 26 | OF101 | ....CA.G..Y.T..AR........ ...-...T..T....-..T...- |
| 27 | TN9 | ....CA.G....T..A......... ...-...T..T....-..T...- |
| 28 | WKS8 | ....CA.G....T..A......... ...-...T..T....-..T...- |
| 29 | ATJP03 | ....CA.R.K..T..A......... ...-...T..T....-..T...- |
| 30 | ACJP03 | W...CA.G....T..A......... ...-...T.YT....-..T...- |
| 31 | ACPP01 | ....CA.G....T..A......... ...-...T..T....-..T...- |
| 32 | ACPP02 | ....CA.G....T..A......... ...-...T..T....-..T...- |
| 33 | G.CRUX | ....CA.G....T..A......... ...-...T..T....-..T...- |
| 34 | GHOPE1 | ....CA.G....T..A......... ...-...T..T....-..T...- |
| 35 | GHOPE2 | ....CA.G....T..A......... ...-...T..T....-..T...- |
| 36 | ATBBO1 | ....CA.G...T..TAC........ ...-......T....-.MT.... |
| 37 | CU13 | .......-.C...ACT......T.. ...ACT.-...T...A-CG.TATGT |
| 38 | CU1 | .......-......TC......... ...-CT.T...AAT..-CT.A.T.C |
| 39 | AABB01/2 | .......-......GC......... ...-CT.T...AAT..-CT.A.T.C |
| 40 | PA5V | .......-......GC......... ...-CT.T...AAT..-CT.A.T.C |
| 41 | AMAD01 | ......A-.....CGC......T.. ...AA..T...A.A..-CT.T.T.. |
| 42 | AMAD06 | ......A-.....CGC......T.. ...AA..T...A.A..-CT.T.T.. |
| 43 | GTPORT | ......A-.....CGC......T.. ...AA..T...A.A..-CT.T.T.. |
| 44 | TC02 | ......A-..A...TTG..C.CG.. ...C.TC.-..A....GCT.T.T-. |
| 45 | P micans | G.GUCUGG..GC.GUGC..CU.GAU C.UG.GC.CUGGGA..GAG.UC.CU |

FIG. 1(1)

| SEQUENCE ID. NO. | STRAIN | 601 … 650 |
|---|---|---|
| 11 | PW06 | CTTGGG--GAT-GCTTCCTTCCTTG GAC-TTACAAGCCCTGACACACACA |
| 12 | PI32 | ......--...-............. ...-..................... |
| 13 | BGt1 | ......--...-............. ...-..................... |
| 14 | AFNFA3.1 | ......--...-............. ...-..................... |
| 15 | GtCA29 | ......--...-............. ...-..................... |
| 16 | AFNFA3.2 | ......--...-............. ...-..................... |
| 17 | AFNFA4 | ......--...-............. ...-..................... |
| 18 | GTMPSHER | ......--...-............. ...-..................... |
| 19 | I72/24#1 | ......--...-............. ...-..................... |
| 20 | OF041 | ..W...--...-R.K.......... ...-..................... |
| 21 | OF051 | ......--...-R.K.......... ...-..................... |
| 22 | PGT183 | T..-.A--.G.T............. .G.-..................... |
| 23 | PE1V | T..-.A--.G.T............. .G.-..................... |
| 24 | PE2V | T..-.A--.G.T............. .G.-..................... |
| 25 | WKS1 | T..-.A--.G.T............. .G.-..................... |
| 26 | OF101 | .C.T.A--.G.T...T..C...... .G.-.....T......G........ |
| 27 | TN9 | .C.T.A--.G.T...T..C...... .G.-.....T......G........ |
| 28 | WKS8 | .C.T.A--.G.T...T..C...... .G.-.Y...T......G........ |
| 29 | ATJP03 | .C.T.A--.G.T...T..C...... .G.-.....T......G........ |
| 30 | ACJP03 | .C.T.A--.G.T...T..C...... .G.-.....T......G........ |
| 31 | ACPP01 | .C.T.A--.G.T...T..C...... .G.-.....T......G........ |
| 32 | ACPP02 | .C.T.A--.G.T...T..C...... .G.-.....T......G........ |
| 33 | G.CRUX | .C.T.A--.G.T...T..C...... .G.-.....T......G........ |
| 34 | GHOPE1 | .C.T.A--.G.T...T..C...... .G.-.....T......G........ |
| 35 | GHOPE2 | .C.T.A--.G.T...T..C...... .G.-.....T......G........ |
| 36 | ATBBO1 | .-.T.T--.G.T...T......... .G.-..G.........G........ |
| 37 | CU13 | G.ACA.AA.G.T.T..T......G. .T.A--.......T.A.....G..T |
| 38 | CU1 | T.GAA.CT.GGC-..A..C.A..A. AG.-............G......AT |
| 39 | AABB01/2 | T.GAA.CT.GGC-..A..C.A..A. AG.-............G......AT |
| 40 | PA5V | T.GAA.CT.GGC-..A..C.A..A. AG.-............G......AT |
| 41 | AMAD01 | TCGAA.GG..AA....A...TT... AG.A..G........T.....TCAG |
| 42 | AMAD06 | TCGAA.GG..AA....A...TT... AG.A..G........T.....TCAG |
| 43 | GTPORT | TCGAA.GG..AA....A...TT... AG.A..G........T.....TCAG |
| 44 | TC02 | ..GT..GG..ATTM.-...C.RCCC TG.-.-G-..T....TG.R.TACAT |
| 45 | P micans | CC.ACAACCUCCCU.CUAAGG--.C U-CA-GCGCUU..........U.-G |

FIG. 1(m)

| SEQUENCE ID. NO. | STRAIN | 651 (end D2 domain <- 678) | |
|---|---|---|---|
| 11 | PW06 | TGCTGGCAAAATGCTTCTGCTTGAC | CCG |
| 12 | PI32 | .............M........... | ... |
| 13 | BGt1 | Y........................ | ... |
| 14 | AFNFA3.1 | ......................... | ... |
| 15 | GtCA29 | ............RM..M........ | ... |
| 16 | AFNFA3.2 | ......................... | ... |
| 17 | AFNFA4 | ......................... | ... |
| 18 | GTMPSHER | ......................... | ... |
| 19 | I72/24#1 | ......................... | ... |
| 20 | OF041 | ......................... | ... |
| 21 | OF051 | ......................... | ... |
| 22 | PGT183 | AT...........T........... | ... |
| 23 | PE1V | AT...........T........... | ... |
| 24 | PE2V | AT...........T........... | ... |
| 25 | WKS1 | AT...........T........... | ... |
| 26 | OF101 | .T....................... | ... |
| 27 | TN9 | .T....................... | ... |
| 28 | WKS8 | .T....................... | ... |
| 29 | ATJP03 | .T.......R............... | ... |
| 30 | ACJP03 | .T....................... | ... |
| 31 | ACPP01 | .T....................... | ... |
| 32 | ACPP02 | .T....................... | ... |
| 33 | G.CRUX | .T....................... | ... |
| 34 | GHOPE1 | .T..........R.....R...... | ... |
| 35 | GHOPE2 | .T....................... | ... |
| 36 | ATBB01 | .T.......C............... | ... |
| 37 | CU13 | ......................... | ... |
| 38 | CU1 | ......................... | ... |
| 39 | AABB01/2 | ......................... | ... |
| 40 | PA5V | ......................... | ... |
| 41 | AMAD01 | .............T........... | ... |
| 42 | AMAD06 | .............T........... | ... |
| 43 | GTPORT | .............T........... | ... |
| 44 | TC02 | C............T........... | ... |
| 45 | P micans | C.A..A.U.A...G..C.AU.C... | ... |

FIG. 1(n)

GENETIC MARKERS AND METHODS OF IDENTIFYING ALEXANDRIUM (DINOPHYCEAE) SPECIES

This is a continuation of application Ser. No. 07/967,637, filed Oct. 28, 1992, now abandoned.

FIELD OF THE INVENTION

This invention relates to genetic markers that distinguish between closely-related species, or strains of toxigenic marine dinoflagellates within the Alexandrium genus and, more specifically, to methods for detecting such toxic organisms.

BACKGROUND OF THE INVENTION

Toxic dinoflagellates of the genus Alexandrium occurring along the northeastern coasts of the United States and Canada pose an important problem in population biology and systematics, as well as a serious economic and public health concern. The organisms responsible for causing the toxic outbreaks have apparently spread from endemic populations in eastern Canada as far south as Long Island over the last few decades (Hayhome, B. A., et al., *Mar. Biol.* 101: 427–435 (1989)). Identification of different populations of these toxic algae is essential in understanding and managing the regional phenomenon.

Toxic red tides along the New England and Canadian coasts result from "blooms" of *Alexandrium fundyense* and *A. tamarense*. These dinoflagellates produce potent neurotoxins which can accumulate in shellfish. Ingestion of contaminated shellfish by human consumers can cause paralysis and in extreme cases death, giving rise to the term "paralytic shellfish poisoning", or PSP. PSP toxins were documented in northern Maine in 1958, New Hampshire and Massachusetts in 1972, Connecticut in 1982, and Long Island in 1986. This has been interpreted as evidence of an introduction, dispersal, and successful colonization of these toxic species into New England's coastal waters from source populations long-established in eastern Canada. Similar expansions in the geographic range of toxic Alexandrium species have occurred in the Pacific northwest, and in other parts of the world. The success of this organism's dispersal and recurrence appear to lie in its ability to undergo a sexual phase of its life cycle and over winter in sediments as a zygotic dormant cell or cyst. In spring, these cysts can germinate, presumably undergo meiotic divisions and resume asexual growth, populating the overlying waters (Anderson and Morel, *Marine Sci.* 8: 279–293 1979; Anderson et al., *Mar. Biol.* 76: 179–189, 1983; Fritz, et al., *J. Phycology* 25: 95–107 1989).

It is now evident that Alexandrium populations throughout the world are not homogeneous in their distribution, but rather consist of sub-populations with different physiological characteristics (Maranda, L., et al., *Estur. Coastal Shelf Sci.* 21: 401–410 (1985); Hayhome, B. A., et al., *Mar. Biol.* 101: 427–435 (1989)) and possible differences with respect to their origin or timing of their dispersal (Anderson, D. M., In Okaichi, T., Anderson, D. M. and Nemoto, T. (Eds.) *Red tides: Biology, environmental science and toxicology.* Elsevier New York, pp. 11–20 (1989). It is also of note that Alexandrium blooms and cyst accumulations can be widespread in some coastal waters, but patchy and localized within shallow embayments and estuaries in other areas (Anderson et al., *Estur. Coastal Shelf Sci.* 14: 447–458 (1982), Schrey et al., 1984, *Estuaries* 7: 472–477 (1984)).

Blooms can thus be considered as "point sources", with little or no exchange or mixing with other Alexandrium populations, or on the other hand, can cover hundreds of kilometers and can be advected far from their origins, providing greater opportunity for gene flow among populations. Toxicity records compiled by the state governments support the concepts of both localized, independently blooming populations and advection of larger blooms. Despite the excellent progress made in understanding Alexandrium bloom dynamics, the source of the cells responsible for a given PSP outbreak and the degree of their genetic homogeneity remain enigmas.

The taxonomy of the armoured, saxitoxin-producing dinoflagellates (historically called the "tamarensis/catenella group") has long been confusing and contentious. For years controversy centered around an appropriate genus designation, and only recently was an international agreement made to use Alexandrium (Steidinger and Moestrup, In: *Toxic Marine Phytophankton,* Ed. by E. Granch; et al., pp. 522–523 (1990)). Although the confusion over genus names appears to be over, there continue to be concerns about species assignments. On one side are those that differentiate species on the basis of small morphological features such as the shapes and positions of certain thecal plates or the presence or absence of pores (Balech, *In: Toxic Dinoflagellates.* Anderson, D. M., et al., (Eds.) Elsevier, New York, pp. 33–38 (1985)). At the other side of the controversy are those who believe the tamarensis/catenalla group represents a single species complex comprised of numerous biochemically-distinct varieties (Taylor, F. J. R. "The taxonomy and relationships of red tide dinoflagellates, *In: Toxic Dinoflagellates.,* Anderson, D. M., et al. (Eds.) Elsevier, New York, pp. 11–26 (1985)); Cembella, A. D. et al., *Biochem. Sys. and Ecol.* 14: 311–323 (1986); and Cembella, A. D., et al., *Biochem. Sys. and Ecol.* 15: 171–186 (1987). The generation of additional, independent criteria for examining different isolates could aid in the settlement of this controversy, and benefit those interested in unifying Alexandrium systematics.

Detailed toxin composition and enzyme electrophoretic studies, in conjunction with traditional, morphologically-based taxonomic analyses, have all been applied to assess the genetic similarity of Alexandrium isolates. Collectively, these markers represent complex character states which are dependent on the coordinated expression of multiple genes and, consequently, require fastidious culturing, harvesting, preparation and analytical procedures to ensure equitable comparisons. Despite such efforts, the delineation of population and taxonomic boundaries within and between Alexandrium species has remained coarse. At present, there is both a lack of specific genetic markers for many Alexandrium strains, as well as international disagreement over the relative importance of morphologically-based taxonomic criteria. This, in turn, has complicated efforts to understand the population dynamics and potential dispersal of these toxic organisms.

SUMMARY OF THE INVENTION

We have discovered that Alexandrium strains can be identified and characterized by detecting the presence of preselected sequences of ribosomal RNA (rRNA) in samples. Particularly useful rRNA sequences are provided by the Large Subunit rRNA genes (LsrDNA). A particularly useful fragment of the LsrDNA including the D1 and D2 Hypervariable Domains (Mitchot et al., *Nucl. Acids Res.* 12: 4259–4279 (1984); Lenaers et al., *J. Mol. Evol.* 29: 40–51

(1989)) has been identified and cloned, having about 700 bp.

Eight distinct sequence types ("ribotypes") of Alexandrium have been identified based on distinct heterogeneities in the rRNA sequences. The presence of a particular type of Alexandrium in a sample of sea water can thus be determined, in accord with the present invention, by detection using a labeled nucleotide probe designed to hybridize with the particular genetic marker rRNA sequence indicative of the particular strain of Alexandrium.

In accord with one embodiment of the invention, regions of substantial homology in the rRNA genes of various species of Alexandrium having similar physical or geographical characteristics are identified, labelled nucleotide probes are provided that substantially hybridize to rRNA produced by the genes that contain the predetermined homologous regions, and the probes are used to assay for the presence of such species. In particular, a fragment of the LsrDNA that includes the D1 and D2 Hypervariable Domains is used to select regions of substantial homology in selected species of Alexandrium.

In a preferred embodiment of the invention, the presence of any Alexandrium species can be determined by detecting the sequence (5'-3') CAUUGGAAUGCAAAGUGGGU (SEQ. ID NO. 1) in a sample using a labelled probe.

In another preferred embodiment of the invention, the presence of a strain of toxic "North American" *A. tamarense/catenella/fundyense* can be determined by detecting the sequence (5'-3') UGGUGGGAGUGUUGCACU (SEQ. ID. NO. 2) in a sample using a labeled probe.

In another preferred embodiment of the invention, the presence of a strain of toxic "North American" *A. tamarense/catenella/fundyense* can be determined by detecting the sequence (5'-3') AUGAUAAGUCUCCUGUGG (SEQ. ID. NO. 3) in a sample using a labelled probe.

In another preferred embodiment of the invention, the presence of a strain of non-toxic "Western European" *A. tamarense* can be determined by detecting the sequence (5'-3') AUCUGUUUUUGUUCCAUGUG (SEQ. ID. NO. 4) in a sample using a labeled probe.

In another preferred embodiment of the invention, the presence of toxic "Temperate Asian" *A. tamarense/catenella* can be determined by detecting the sequence (5'-3') GCUGCAAGUGCAAUAAUU (SEQ. ID. NO. 5) in a sample using a labeled probe.

Examples of preferred nucleotide probes include sequences containing the following nucleotide sequences (5'-3'):

ACCCACTTTGCATTCCAATG (SEQ. ID. NO. 6)
AGTGCAACACTCCCACCA (SEQ. ID. NO. 7)
CCACAGGAGACTTATCAT (SEQ. ID. NO. 8)
CACATGGAACAAAAAGACAT (SEQ. ID. NO. 9)
AATTATTGCACTTGCAGC (SEQ. ID. NO. 10)

Preferably, a probe will have at least 75% homology of hybridization with the sequence to be detected in a particular Alexandrium.

BRIEF DESCRIPTION OF THE DRAWINGS

FIGS. 1(*a*)–1(*n*) illustrate the LsrDNA sequence alignment for LsrDNA fragments from various Alexandrium strains.

DETAILED DESCRIPTION OF THE INVENTION

In accord with the present invention, LsrDNA can provide distinct molecular markers for Alexandrium species.

A fragment of the large-subunit ribosomal RNA gene (LsrDNA) from various strains of the marine dinoflagellates Alexandrium has been cloned and sequenced in order to assess the organisms' inter- and intraspecific relationships. Analysis of the LsrDNA has revealed hypervariable domains which provide highly specific signature sequences useful in identifying and detecting genetically similar populations.

Figure 2:
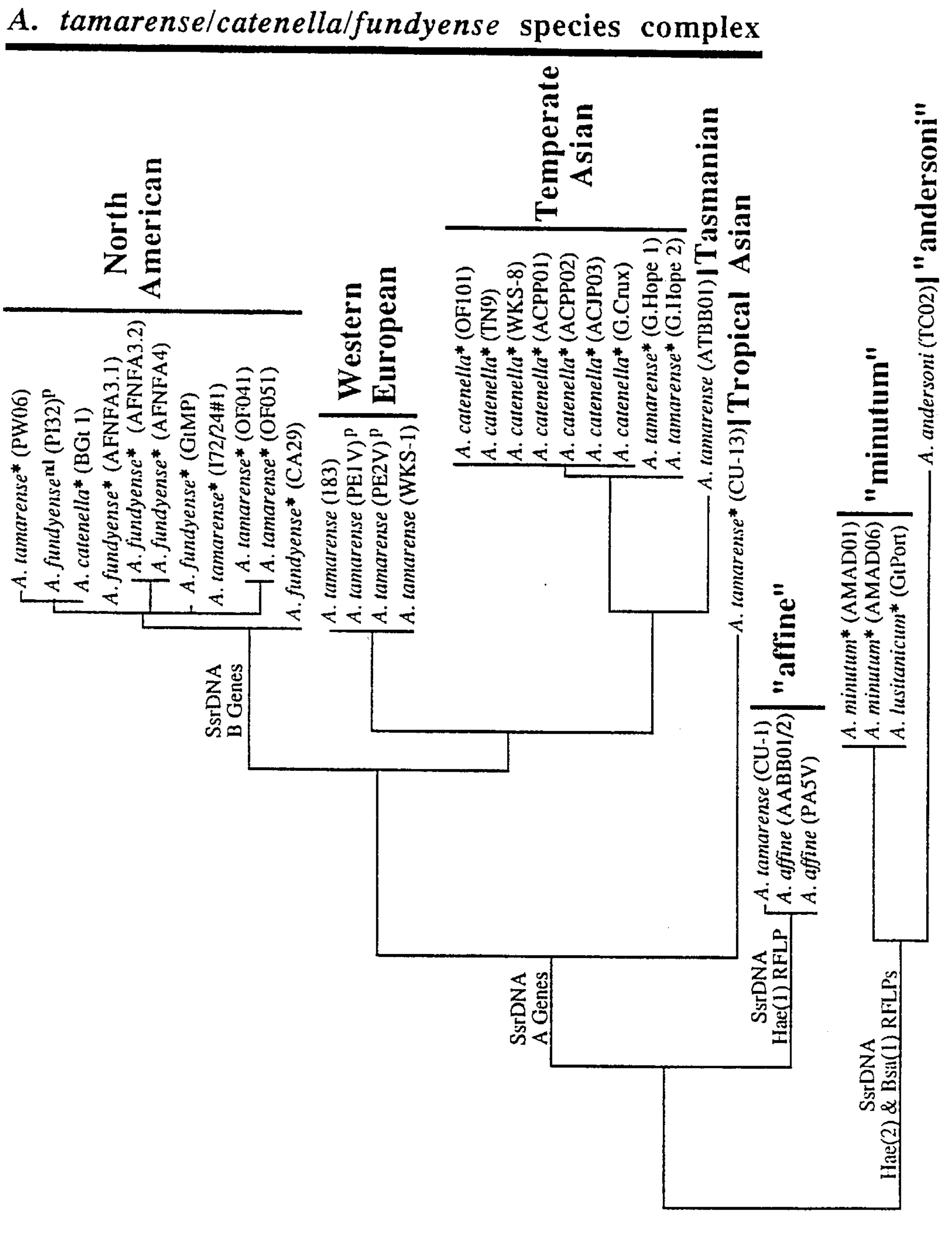
FIG. 2 is a Phylogenetic tree based on the aligned sequences illustrated in FIGS. 1(*a*)–1(*n*).
Figure 3:
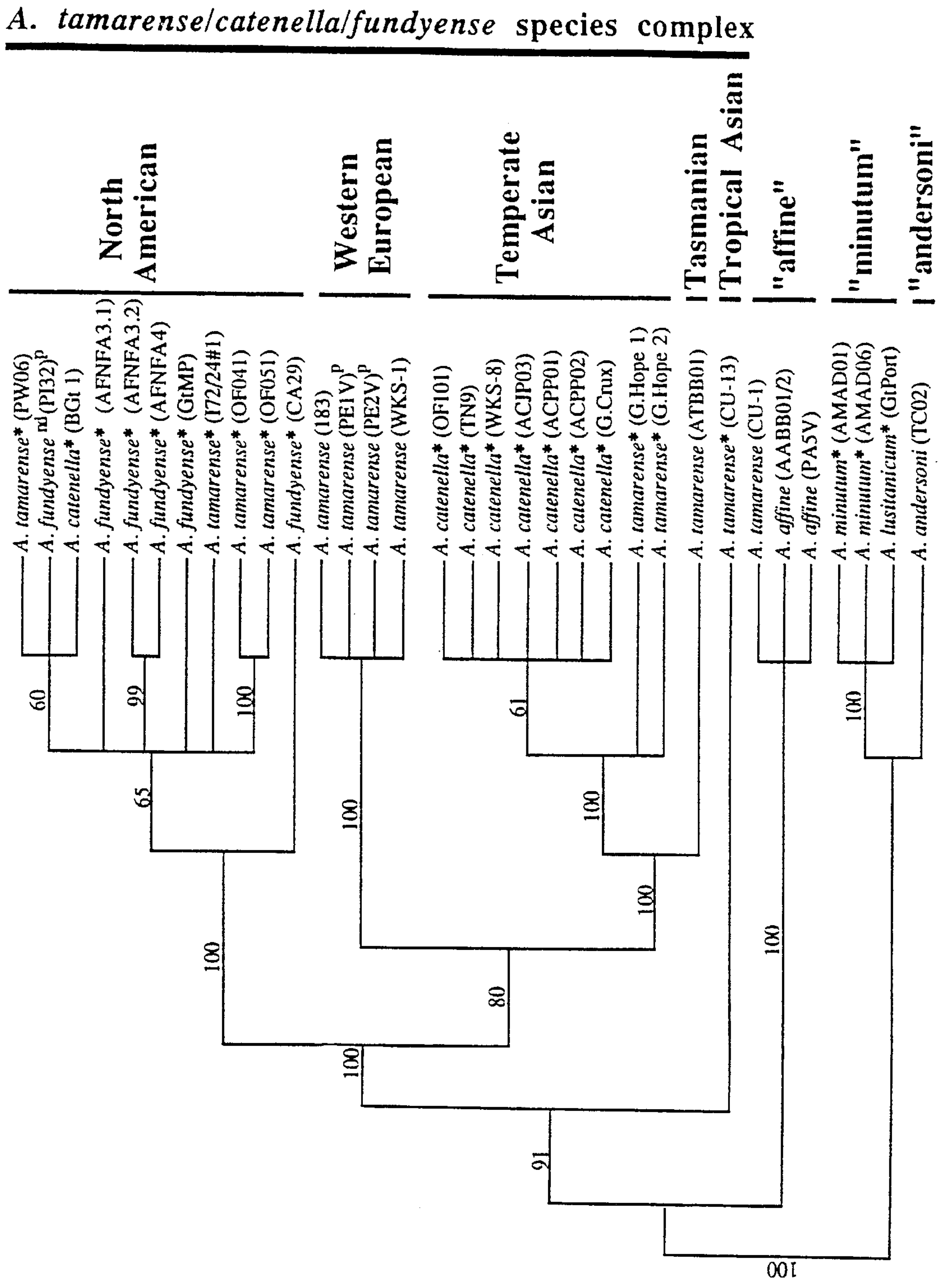
FIG. 3 is a Parsimony bootstrap consensus tree based on 500 resamplings of the aligned sequences illustrates in FIGS. 1(*a*)–1(*n*).

Sequence analysis of the LsrDNA fragments from geographically-diverse representatives of the *Alexandrium tamarense/catenella/fundyense* species complex revealed the existence of at least five genetically-distinct strains (FIGS. 2 and 3, Table 1). These strains ("ribotypes") do not strictly correspond to morphospecies designations, indicating that the morphological features of *A. tamarense, A. catenella* and *A. fundyense* are less specific indicators of the organisms' relationships than are their LsrDNA sequences. Particular regional populations of *A. tamarense, A. catenella* and *A. fundyense* do not appear to have distinct sequence characteristics. Given the isolates examined thus far, *A. tamarense, A. catenella* or *A. fundyense* collected from the same geographic region appear the most similar regardless of morphospecies designations, whereas those from geographically-isolated populations are more divergent even when the same morphospecies are compared. *Alexandrium tamarense* and *A. catenella* from Japan are a notable exception to this general trend, possibly because some *A. tamarense* are the descendants of introduced species (see below). LsrDNA sequences from *A. affine, A. minutum, A. lusitanicum* and *A. andersoni* show that these organisms are distinct from the *A. tamarense/catenella/fundyense* complex. Furthermore, *A. affine* is clearly separable from the *A. minutum/lusitanicum/andersoni* group. Likewise, *A. andersoni* differs from *A. minutum/lusitanicum,* but *A. minutum* and *A. lusitanicum* are indistinguishable (FIGS. 2 and 3, Table 1). *Alexandrium minutum, A. lusitanicum* and *A. andersoni* may be members of yet another Alexandrium species complex. Thus, LsrDNA sequences are useful species- and strain-specific (or population-specific) genetic markers.

LsrDNA sequences from globally-distributed representatives of *A. tamarense/catenella/fundyense* (1) can appear similar or divergent—irrespective of an isolates' morphotype—and (2) and are non-uniformly distributed throughout the world, indicates that different regional populations can have unique combinations of morphotypes and genotypes. The "North American", "Temperate Asian" and "minutum" groups thus far consist exclusively of toxic isolates. In contrast, the "Western European" group encompasses only non-toxic organisms. Single terminal taxa classified as "Australian", "Tropical Asian" and "andersoni" are also non-toxic. Preliminarily, this suggests that an organisms's ability to produce toxin is correlated with its LsrDNA phylogenetic lineage; that is, its evolutionary history (FIG. 2 and Table 1).

In accord with the present invention, the presence of strains of Alexandrium belonging to a particular preselected grouping in a sample of sea water can be determined by contacting the rRNA in the sample, with a preselected nucleotide probe capable of selectively hybridizing to the Alexandrium rRNA from said grouping, and detecting the hybridized probes. Probes useful herein can be any convenient length conventionally used. Preferably, the probe is in the range of 12 to 50 bases and, more preferably, in the range of 15 to 35 bases. An rRNA sequence of predetermined length in the desired Alexandrium grouping is selected which has a high degree of homogeneity, preferably close to 100%. The nucleotide sequence complimentary to the selected rRNA sequence is determined, and the oligodeoxyribonucleotide or oligoribonucleotide probe is synthesized by conventional techniques well known to those skilled in the art.

Such probes can be used to differentiate between preselected Alexandrium groupings by selecting appropriate rRNA sequences for detection. For example, the Alexandrium genus can be detected by selecting a sequence around base 250 (FIGS. 1(*e*), 1(*f*)); the "North American" *A. tamarense/catenella/fundyense* grouping (FIG. 2) can be detected by selecting a sequence around base 402 or base 509 (FIGS. 1(*h*), 1(*i*), 1(*k*)); and the "Temperate Asian" *A. tamarense/catenella* grouping (FIG. 2) can be detected by selecting a sequence around base 450 (FIGS. 1(*i*), 1(*j*)).

To enable detection of the hybridized probes, the probes can be labelled with a radioactive, enzymatic or other type of label by any conventional procedure. Such labels and methods for attachment are well known to those skilled in the art. Preferably, a label that can be detected by a colorimetric or other visible change is used.

The following example is provided to further illustrate the invention.

EXAMPLE 1

Materials and methods

Cultures used in this study listed in Table 1 represent a variety of Alexandrium morphospecies, and some of their globally-distributed populations. All were maintained in f/2 medium as modified and described by Anderson et al., *J. Phycol.* 20: 418–425 (1984). Total nucleic acids from each culture were isolated, quantified and stored as described.

Nucleic Acid Extraction

Approximately 10–15 ml of a mid-log culture were harvested by gentle centrifugation and the cell pellet resuspended in approximately 200 μl of autoclaved Milli-Q water (Millipore Corp.) at room temperature. The cell slurry was

TABLE 1

Strain numbers, species designations, isolation locales, toxicity, number of LsrDNA clones isolated and sequenced, length of PCR-amplified LsrDNA fragment and sources of Alexandrium cultures.

| Geographic Block | Strain[a] | spp. Designation | Isolation Locale | Toxic?[c] | #LsrDNA Clones Isolated[d] | Length of LsrDNA Fragment[e] |
|---|---|---|---|---|---|---|
| North America | | | | | | |
| W. Coast | PW06* | *A. tamarense* | Port Benny, Alaska | yes | 5, 7 | 668 |
| | P132* | *A. fundyense* | Porpoise Isl., Alaska | nd | 7 | 668 |
| | BGt 1* | *A. catenella* | Russian River, CA | yes | 10 | 668 |
| E. Coast | AFNFA3* | *A, fundyense* | Newfoundland | yes | 8 | 666/668 |
| | AFNFA4* | *A. fundyense*[b] | Newfoundland | yes | 11 | 666/668 |
| | Gony.# 7 | *A. fundyense* | Bay of Fundy | yes | 14 | 666/668 |
| | Gt 429 | *A. fundyense* | Ipswitch Bay, MA | yes | 13 | 666/668 |
| | Gt CA29* | *A. fundyense* | Cape Ann, MA | yes | 7 | 666/668 |
| | GTMP* | *A. fundyense* | Orleans, MA | yes | 12 | 666/668 |
| | GtPP01 | *A. tamarense* | Falmouth, MA | yes | 13 | 666/668 |
| | GtPP06 | *A. tamaense* | Falmouth, MA | yes | 10 | 666/668 |
| | Gt CN16 | *A. tamarense* | Groton, CN | yes | 9 | 666/668 |
| | Gt L121 | *A. tamarense* | Babylon, NY | yes | 12 | 666/668 |
| | TC02* | *A. andersoni* | Eastham, MA | no | 11 | 661 |
| W. Europe | | | | | | |
| U.K. | Pgt183 | *A. tamarense* | Plymouth, U.K. | no | 7 | 669 |
| Spain | PE1V* | *A. tamarense*[b] | Galicia, Spain | no* | 12 | 669 |
| | PE2V* | *A. tamarense*[b] | Galicia, Spain | no | 14 | 669 |
| | PA5V* | *A. affine* | Galicia, Spain | yes | 12 | 676 |
| Portugal | GtPort* | *A. lusitanicum* | Portugal | yes | 9 | 671 |
| Japan | | | | | | |
| North | OF041* | *A. tamarense* | Ofunato Bay, Japan | yes | 13 | 666/668 |
| | OF051* | *A. tamarense* | Ofunato Bay, Japan | yes | 10 | 666/668 |
| | OF101* | *A. catenella* | Ofunato Bay, Japan | yes | 10 | 669 |
| South | TN-9* | *A. catenella* | Tanabe Bay, Japan | yes | 10 | 669 |
| | WKS-1* | *A. tamarense* | Tanabe Bay, Japan | no | 12 | 669 |
| | WKS-8 | *A. catenella* | Tanabe Bay, Japan | nd | 10 | 669 |
| Gulf of Thailand | CU-1* | *A. tamarense* | Gulf of Thailand | no | 10 | 666 |
| | CU13* | *A. tamarense* | Gulf of Thailand | yes | 14 | 671 |
| Australia | | | | | | |
| mainland | ACPP01* | *A. catenella* | Port Phillip Bay, Australia | yes | 12 | 669 |
| | ACPP02* | *A. catenella* | Port Phillip Bay, Australia | yes | 9 | 669 |
| | ACPP03 | *A. catenella* | Port Phillip Bay, Australia | yes | 11 | 669 |
| | ACPP09 | *A. catenella* | Port Phillip Bay, Australia | yes | 11 | 669 |
| | AMAD01* | *A. minutum* | Port River, Australia | yes | 12 | 669 |
| | AMAD06* | *A. minutum* | Port River, Australia | yes | 14 | 676 |
| Tasmania | ATBB01* | *A. tamarense* | Bell Bay, Tasmania | no* | 12 | 676 |
| | AABB01/2* | *A. affine* | Bell Bay, Tasmania | no | 10 | 669 |
| ballast | 172/21 #2 | *A. tamarense* | Muroran, Japan (N)[g] | yes | 10 | 671 |
| water | 172/2 #4* | *A. tamarense* | Muroran, Japan (N)[g] | yes | 7 | 666/668 |
| | ACJP03* | *A. catenella* | Kashima, Japan (S)[g] | yes | 10 | 666/668 |

TABLE 1-continued

Strain numbers, species designations, isolation locales, toxicity, number of LsrDNA clones isolated and sequenced, length of PCR-amplified LsrDNA fragment and sources of Alexandrium cultures.

| Geographic Block | Strain[a] | spp. Designation | Isolation Locale | Toxic?[c] | #LsrDNA Clones Isolated[d] | Length of LsrDNA Fragment[e] |
|---|---|---|---|---|---|---|
| | G. Crux* | *A. catenella* | Singapore[h] | yes | 11 | 669 |
| | G. Hope 1* | *A. tamarense* | Samchonpo, S. Korea[g] | yes | 5 | 669 |
| | G. Hope 2* | *A. tamarense* | Samchonpo, S. Korea[g] | yes | 4 | 669 |

[a)]strain listings currently used in the D. M. Anderson culture collection; "*" indicates isolates whose sequences were used to construct the phylogenetic trees (FIGS. 2 and 3); all cultures are clonal except for BGt 1, GtMP, PE1V, PE2V, G. Hope 1 and G. Hope 2
[b)]provisional species designations
[c)]determined by mouse bioassay and/or HPLC analysis; "nd" indicates "not determined (or unknown); "*" may contain trace amounts of toxin
[d)]number of LsrDNA fragment clones isolated from a given culture and pooled prior to sequencing; LsrDNA fragments from PW06 were cloned on two separate occasions
[e)]sequence length (base pairs) of the PCR-amplified LsrDNA fragment; cultures harboring the 590–591 heterogeneity are denoted "666/668"
[f)]individuals who suppled the culture
[g)]presumed origin (Hallegraeff and Bolch, 1992)
[h)]hailing port of vessel - origin of ballast water uncertain (Hallegraeff and Bolch, 1992)

transferred to a 1.5 ml sterile microcentrifuge tube and adjusted to contain: 1% SDS, 10 mM EDTA (pH 8.0), 10 mM Tris HCl (pH 7.5) and 10 mM NaCl in a final volume of 250 μl. Nucleic acids in this solution were purified by extracting once with tris-buffered phenol, 2–3 times with phenol:chloroform: isoamyl alcohol (PCI; 24: 24:1) and once with chlorform: isoamyl alcohol (CI; 24:1; Ausubel et al. 1987). Total nucleic acids were precipitated by the addition of 2 volumes of ice-cold 100% ethanol and 1/10 volume 3M NaOAc (pH 5.0), followed by chilled at –20° C. for at least hours. The precipitate was collected by centrifugation in a chilled (~4° C.) Sorvall Microfuge at ~12,000×g for 15 minutes, supernatant was decanted, and the nucleic acid pellet rinsed with 80% EtOH for at least 30 minutes at –20° C. After rinsing, the sample was spun again, the EtOH wash removed, the pellet briefly air-dried and then resuspended inn 10–50 μl of TE (10 mM Tris-HCl pH 7.5, 1 mM EDTA pH 8.0). The concentration of DNA was determined by diluting an aliquot and reading its absorbence at 260 nm (Ausubel et al. 1987 supra). DNA samples were stored at—20° C. until needed.

Polymerase Chain Reaction (PCR Amplifications)

Approximately 700 base pairs of the LsrDNAs were PCR-amplified (Saiki et al, *Sci.* 239: 487–491 (1988)) using primers targeted towards conserved elements at positions 24–45 ("D1R" (forward); 5'ACCCGCTGAATTTAAGCATA3' (SEQ. ID. NO. 46)) and 733–714 (("D2C" reverse); 5'CCTTGGTCCGTCTTTCAAGA3' (SEQ. ID. NO. 47)), relative to the *Prorocentrum micans* LsrRNA (Lenaers et al., *J. Mol. Evol.* 29: 40–51 1989). This fragment encompasses the evolutionarily variable domains D1 and D2. Amplifications were carried out using a Perkin Elmer Cetus DNA Thermal Cycler and Perkin Elmer GeneAmp PCR Core Reagents as recommended by the manufacturers. Amplifications were typically carried out as follows: denaturing at 92° C.—1.5 min; cooling to 45° C.—30 sec; annealing at 45° C.—1.5 min; warming to 72° C.—2.0 min. This cycle was repeated 30 times with an auto extension (5 sec/cycle). PCR reactions for a given DNA preparations were done in duplicate or triplicate. Optimal, final concentrations of primers were found to be 0.1 μM using 3mM $MgCl_2$ and 1 ng of total DNA (when necessary, dilutions of DNA were made in autoclaved Milli-Q water). Following amplification, replicate reactions were pooled and purified by extracting once with PCI and once with CI. The products were concentrated by standard EtOH precipitation and resuspended in 10–50 μl of TE (pH 7.5). Amplified LsrDNAs were stored at –20° C.

Cloning of LsrDNA

LsrDNA fragments were cloned using Invitrogen's T/A cloning kit (cf. Holton et al. *Nucl. Acids Res.* 19: 1156 (1991), Marchuck et al. *Nucl. Acids. Res.* 19: 1154 (1991)) according to the recommendations of the manufacturers. Generally, 16 bacterial clones potentially containing plasmids with a LsrDNA insert (i.e., white colonies) were screened for each dinoflagellate examined. In addition, a bacterial clone known to contain a plasmid without an insert (i.e. blue colony) was also processed. Each bacterial clone was inoculated into 2 ml of L Broth (Ausubel et al., 1987, supra) containing 50 μg/ml kanamycin and was grown overnight at 37° C. with vigorous shaking. Plasmid preparations for each clone were carried out with 1.5 ml of the overnight culture using the modified Birnboim procedure as described by (Ausubel et al., 1987, supra). The remaining 0.5 ml of culture was kept at 4° C. during the plasmid isolation and screening procedure. Initial plasmid precipitates were rinsed in 1 ml of ice-cold 80% EtOH for at least 30 minutes at –20° C. and spun at 12,000×g for 10 min in a cold (~4° C.) Sorvall microfuge. Supernatants were removed by vacuum aspiration and the pellet air dried for 5–10 minutes. Following this, the plasmids were resuspended in 50 M TE (7.5)+DNase-free RNase A (1 ml TE+10 μl 10 mg/mL Rnase A (supplied and prepared as directed by Sigma). After removing an aliquot for restriction digestion (see below), the plasmids were stored at –20° C.

Selection of LsrDNA Clones

One μl of each resuspended plasmid was digested with HindIII (New England Biolabs) in a final volume of 10 μl. Products of the digestions were resolved on 0.7% agarose gels using 1XTBE buffer (Ausubel et al. 1987, supra). HindIII cleaves once within the cloning vector and had no sites within any of the LsrDNA fragments examined. Clones containing a single LsrDNA insert were identified by comparing their mobility to size standards and the negative control (i.e., blue clone) plasmid. Positive plasmid clones were stored separately at –20° C. The remaining portion of corresponding bacterial cultures were cryo-preserved by addition of an equal volume of freeze down buffer (1% (w/v) yeast extract, 10% (v/v) dimethylsulfoxide, 10% (v/v) glycerol, 0.2M $K_2HPO_4/NaH_2PO_4$ (pH 7.0) and storage at –80° C.

Sequencing of LsrDNA Clones

Several precautions were taken in order to minimize sequencing errors: 1) two to three replicate PCR amplifications were pooled prior to cloning; 2) multiple LsRDNA clones from each Alexandrium isolate were pooled prior to sequencing to gauge the homogeneity of the products and identify the locations of ambiguities or length heterogeneities; and, 3) both strands of the cloned molecules were sequenced to aid the accuracy of the determinations (Sogin, "Amplification of ribosomal RNA genes for molecular evolution studies," In: Innis, M. A. et al. (Eds.), *PCR protocols: A guide to methods and applications,* Academic Press, pp. 307–314 (1990)). In some cases where heterogeneities and ambiguities were observed, individual clones from a given isolate were individually sequenced.

Template denaturation.

Aliquots of each positive LsrDNA clone for a given dinoflagellate strain were pooled to yield a final volume of 120 μl in a 1.5 mL microcentrifuge tube. The plasmid pool was denatured with the addition of 120 μl of 0.6N NaOH, gentle mixing and incubation at room temperature for 5 minutes. Denatured templates were neutralized and precipitated by adding 9 μl of 2M $NH_4OAc$ (pH=4.5) and 900 μl of 100% ethanol (EtOH). This solution was vortexed, immediately divided among four separate 0.5 ml tubes (~290 μl/tube) and chilled at −20° C. for at least 2 hours. Each tube contains approximately 30 μl (~1 μg) of denatured plasmid, an amount empirically found to give excellent sequencing results. When analyzing single clones 10–30 μl of an individual plasmid preparation was used per sequencing reaction, denaturation and precipitation were carried out in a single 0.5 ml tube, and volumes of HaOH, $NH_4OAc$ and EtOH were adjusted accordingly. Denatured plasmid precipitates were collected by centrifugation in a chilled (4° C.) Sorvall microfuge at 12,000×g for 10–15 minutes. Supernatant was discarded, and the pellet rinsed in 70% EtOH for at least 30 minutes at −20° C. On the day plasmids were to be sequenced, the precipitate was once again collected by centrifugation, as much supernatant was removed as possible, and pellets were allowed to air dry, but not to completion. The tubes were then tightly capped and stored at 4° C. until needed.

All sequencing reactions were carried out using united States Biochemical (USB) Corp. Sequenase version 2.0 sequencing kit reagents and Amersham DATP ($\alpha^{35}S$) label (10 μCi/μl). Both strands of the LsrDNA inserts were sequenced using the amplification primers ("D1R" (forward) and "D2C" (reverse)), and two internal primers, "D1C" (reverse; 5'ACTCTCTTTTCAAAGTCCTT3' (SEQ. ID. NO. 48); corresponds to *Prorocentrum micans* LsrRNA positions 388–369;) and "D2Ra" (forward; 5'TGAAAAGGACTTTGAAAAGA3' (SEQ. ID. NO. 49); corresponds to *P. micans* LsrRNA positions 345–364)). "Forward" reactions give products whose sequence is rRNA-like, while "reverse" reactions give products whose sequence is the complement of the rRNA.

Primer Hybridization and preparation of Labellinq Mix.

The denatured, precipitated plasmid clones were resuspended with 8 μl primer (0.5 pmol/μl in 10 mM Tris HCl pH=7.5) and 2 μl reaction buffer (USB), mixed, and incubated for ~10 minutes at 37° C. During primer annealing, ice-cold labelling mix for 3 sequencing reactions was prepared by combining: 2.1 μl $ddH_2O$, 3.0 μl 10 mM DTT (USB), 65.0 μl labelling mix (USB; diluted 1:4 with $ddH_2O$, 3.0 μl dATP[$a^{35}S$] (10 μCi/μl), 1.0 μl Sequenase v 2.0 (USB) and 0.5 μl pyrophosphatase (USB); Sequenase and pyrophosphatase were added immediately prior to the completion of the hybridization reactions.

Labelling and termination reactions.

5 μl of labelling mix was added to the 10 μl hybridization reaction, mixed by gentle pipetting and incubated for 1 minute at room temperature. Afterwards, 3.5μl of this solution was added to 2.5 μl of each ddNTP (USB), and allowed to incubate at 37° C. for 10 minutes. Sequencing reactions were terminated by the addition of 4 μl stop mix (USB). Typically, 3 sequencing reactions were carried out in quick succession with overlaps in their termination reactions. Reactions were stored no longer than several days at −20° C. before polyacrylamide gel electrophoresis.

Sequencing Gel Electrophoresis

Products of the sequencing reactions were resolved on 6% polyacrylamide (19:1 acrylamide:bis-acrylamide, 8.3M Urea, 1× TBE gels using a BioRad Sequigencell apparatus. In order to improve resolution of the bands, the top buffer chamber was filled with 0.5×TBE and the bottom chamber filled with 1×TBE. Gels were pre-electrophoresed with a constant power setting until reaching ~50° C. During the pre-electrophoresis, sequencing reactions were thawed on ice, heated to 80° C. for 3 minutes and immediately returned to ice. Approximately 2.5 μl of each reaction was loaded per lane and run until the bromophenol blue dye had migrated roughly ⅓ the length of the gel. Electrophoresis was then briefly terminated while 200 ml (½ volume) of 3M NaOAc (½ volume) of 3M NaOAc (pH 5.0) was added to the bottom buffer chamber. Electrophoresis was resumed and the constant power setting adjusted as required to maintain a surface plate temperature of ~50°–55° C. Electrophoresis was terminated when the xylene cyanol dye front had migrated to within 10–12 cm from the bottom of the gel. Gels were fixed in 10% methanol/10% glacial acetic acid for 30 minutes, dried onto Whatman 3 MM paper at 80° C. for 45 minutes using a Sorvall sequencing gel dryer with applied vacuum, and then exposed to either XAR-5 or XRP-5X- ray film (Kodak). Exposures ranging from overnight to 2 days were found to be optimal. A typical run yielded approximately 300–350 readable nucleotides.

Sequence Analysis

Sequence determinations for a given dinoflagellate culture were compiled using PAUP 3.0 (Swofford 1991). Sequences from each isolate were then aligned with the help of conserved elements interspersed throughout the length of the molecules (FIGS. 1(*a*)–1(*n*). The alignment was subjected to a variety of phylogenetic analyses using heuristic methods (PAUP 3.0 (Phylogenic analysis using parsimony; computer program and documentation distributed by the Illinois Natural History Survey, Chicago, Ill.); Swofford 1991). The phylogenetic tree shown in FIG. 2 was constructed using the following parameters: all characters weighted equally; sequence gap=missing data; stepwise addition; closest addition sequence; 1 tree held at each step during stepwise addition; tree-bisection-reconnection (TBR) branch-swapping performed; MULPARS option in effect; steepest descent option not in effect; maxtrees=200; branches having maximum length zero collapsed to yield polytomies; topological constraints not enforced; trees unrooted; multi-state taxa interpreted as uncertainty; outgroup taxa defined as AMAD01, AMAD06, GtPort and TCO2; and, ACCTRAN character state optimization. Bootstrap analysis (Felsenstein, Evolution 38: 16–24 1985); 500 rounds)) of the alignment was also carried out same parameters as above, except that maxtrees=15 per replicate bootstrap (FIG. 3).

FIGS. 1(*a*)–1(*n*) illustrate the corresponding BDNA sequences for LsrDNA sequence alignment for the listed Alexandrium strains (see Table 1 for species designations and isolation locales). Alignment position 1 corresponds to *P. micans* LsRNA position 45 (Lenaers et al. 1989, supra). PW06 (*A. tamarense,* Alaska) is used as the reference sequence; all equivalent positions are indicated by a period.

Dashes represent inserted alignment gaps. Some organisms contain a TG length heterogeneity (at position 590–591) and are shown with the deletion, as denoted by "**;" these cultures also contain LsrDNAs that do not have this deletion. Two sequences for AFNFA3 (*A. fundyense,* Newfoundland) are shown: AFNFA3.1 is similar to PW06 at positions 106–110 and does not have the 590–591 TG deletion. AFNFA4 (*A. fundyense,* Newfoundland) contains the same two sequences, but is shown here as the AFNFA3.2-like variant. Approximate boundaries of the D1 and D2 hypervariable domains are noted. Sequence ambiguities are reported using standard IUPAC nomenclature (R=A or G; Y=C or T; M=C or A; K=G or T; W=A or T).

FIG. 2 is a Phylogenetic tree inferred from the aligned Alexandrium LsrDNA sequences (generated by PAUP 3.0, Swofford 1991, supra). *Alexandrium minutum, A. lusitanicum* and *A. andersoni* were defined as the outgroup since they all share a common SsrDNA restriction pattern and are the most divergent relative to those isolates within the *A. tamarense/catenella/fundyense* species complex. Branch lengths reflect the relatedness of the sequences relative to PW06. "North American," "Western European," "Temperate Asian", "Tasmanian," "Tropical Asian," "affine," "minutum" and "andersoni" are proposed ribotype designations given to branch termini. Toxic isolates are donoted by "*;" "nd" refers to "toxicity not determined;" "p" indicates "preliminary species designations." Ensemble statistical indices are as follows: consistency index (CI) excluding uninformative characters=0.806; homoplasy index (HI) excluding uninformative characters=0.194; retention index 9RI)=0.948; rescaled consistency index (RC)=0.794 (cf. Swofford 1991, supra).

FIG. 3 is a Parsimony bootstrap consensus tree inferred from 500 resamplings of the aligned Alexandrium LsrDNA sequences (generated by PAUP 3.0, Swofford 1991, supra). Numbers indicate the frequency (%) that taxa to the right of the value were found to group together. Proposed ribotypes as listed in FIG. 2 are also shown.

Results

Amplification, Cloning, Sequencing and Alignment of LsrDNA Fragments

Agarose gel electrophoresis of the PCR-amplified portion of the LsrDNAs typically revealed homogeneous products approximately 700 bp in length. Direct cloning of these molecules yielded an average of 10 positive LsrDNA clones (range 4–14) for each Alexandrium isolate examined (Table 1). LsrDNAs cloned from different Alexandrium isolates vary slightly in length (Table 1). In some cases, the LsrDNAs from a single isolate also contained length heterogeneities and sequence ambiguities (FIGS. 1(*a*)–1(*n*). The most dramatic example of length heterogeneities were found in all cultures of *A. tamarense* and *A. fundyense* from eastern North America, two Japanese *A. tamarense* from Ofunato Bay (OFO41 and OF051) and two ballast water *A. tamarense* (I72/21 #2, I72/21 #4; Table 1). LsrDNA clones from these organisms display an identical two base pair length heterogeneity (TG deletion) as positions 590–591 (FIG 1(*f*)). All isolates that harbor this heterogeneity contain at least two, distinct copies of the LsrDNA: those which carry the 590–591 TG deletion, and those that do not.

Eight distinct classes of sequences, or "ribotypes," were found among the thirty three Alexandrium cultures compared (FIG. 3). The tree topology and significance of branching patterns were examined in several ways. First PAUP outputs of "ensemble statistical indices" (Swofford, supra) were considered to gauge the "fit" of the sequence data and the tree topology. The tree shown in FIG. 3 has relatively high values of consistency indices (consistency index (CI) excluding uninformative characters=0.806; rescaled consistency index (RC)=0.794) and a low degree of homoplasy [homoplasy index (HI) excluding uninformative characters=0.194], suggesting a high degree of congruence between the resolution of Alexandrium groups and their sequence characteristics. Secondly, consensus trees were constructed to evaluate the Alexandrium groupings common among "rival" (i.e., equally parsimonious) trees found in the search. In all cases (strict, Adams and majority-rule) the consensus trees revealed the same associations between cultures as are noted in FIG. 3, indicating that all of the rival trees resolved the Alexandrium sequences in a similar fashion (data not shown). Thirdly, the tree building program was also run using "simple," "random" and "as is" addition sequences (Swofford, supra), and all resulted in trees identical to that shown in FIG. 3. Finally, bootstrap analysis was performed as a statistical test of branching patterns (Felsenstein, supra). Results of this test (FIG. 3) also support the existence of at least eight Alexandrium ribotypes as proposed in FIG. 2.

Definition of Alexandrium Ribotypes

Five of the ribotypes serve to subdivide members of the *Alexandrium tamarense/catenella/fundyense* species complex (FIGS. 2 and 3). With the exception of one non-toxic *A. tamarense* from Thailand (CU-1; now known to be *A. affine*), the three remaining ribotypes were associated with cultures that clearly differ morphologically from the *A. tamarense/catenella/fundyense* group; these three distinct sequences are typified by: 1) *A. affine;* 2) *A. minutum* and *A. lusitanicum;* and, 3) *A. andersoni.* LsrDNAs from *A. minutum* and *A. Lusitanicum* are identical.

The five distinct *Alexandrium tamarense/catenella/fundyense* ribotypes were named with reference to the geographic origin of the isolates: "North American," "Western European" and "Temperate Asian" designations reflect the origins of the majority of cultures within each cluster; "Tasmanian" and "Tropical Asian" designations reflect the origins of single *A. tamarense* cultures. Alexandrium species designations were used to identify the three remaining ribotypes: "affine" and "minutum" were chosen for two of these since their representatives are the most prominent within their respective clusters; "andersoni" was chosen to delineate the final ribotype, reflecting both its unique LsrDNA sequence and the isolate's taxonomic classification.

The invention has been described in detail with reference to preferred embodiments thereof. However, it will be appreciated that, upon consideration of the specification including the examples and drawings, those skilled in the art may make modifications and improvements within the spirit and scope of the invention. For example, probes can be designed to hybridize to either rRNA or rDNA containing the preselected region of homology.

We claim:

1. A method for detecting the presence of a particular type of Alexandrium in a sample, the method comprising:

preselecting a region in the D2 hypervariable domain of the Large subunit rRNA genes of a plurality of species of the particular type of Alexandrium to be detected, the region specifically identifying that type of Alexandrium;

providing a composition consisting essentially of a labelled nucleotide probe consisting of a nucleotide sequence that hybridizes to rDNA containing the preselected region or to the ribosomal RNA produced by the genes containing the preselected region in the rRNA genes;

preparing rRNA from a sample containing a type of Alexandrium;

contacting under hybridization conditions the composition containing the labelled nucleotide probe with the rRNA obtained from the sample; and detecting the presence of hybridized labelled probes indicative of the presence of the particular type of Alexandrium.

2. A method for detecting the presence of toxic "North American" *A. tamarense, A. catenella* and *A. fundyense* in accord with claim 1, wherein the composition consists essentially of a labelled nucleotide probe consisting of the sequence (5'-3') AGTGCAACACTCCCACCA (SEQ. ID. NO. 7).

3. A method for detecting the presence of toxic "North American" *A. tamarense, A. catenella* and *A. fundyense* in accord with claim 1, wherein the composition consists essentially of a labelled nucleotide probe consisting of the sequence (5'-3') CCACAGGAGACTTATCAT (SEQ. ID. NO. 8).

4. A method for detecting the presence of non-toxic "Western European" *A. tamarense* in accord with claim 1, wherein the composition consists essentially of a labelled nucleotide probe consisting of the sequence (5'-3') CACATGGAACAAAAAGACAT (SEQ. ID. NO. 9).

5. A method for detecting the presence of toxic "Temperate Asian" *A. tamarense* and *A. catenella* in accord with claim 1, wherein the composition consists essentially of a labelled nucleotide probe consisting of the sequence (5'-'3) ATTTATTGCACTTGCAGC (SEQ. ID. NO. 10).

6. A method for detecting the presence of a species of Alexandrium in a sample, the method comprising:

preselecting a region in the D2 hypervariable domain of the Large subunit rRNA genes of a plurality of Alexandrium species selected from a variety of geographic locations, the region specifically identifying that type of Alexandrium;

providing a composition consisting essentially of a labelled nucleotide probe consisting of a nucleotide sequence that hybridizes to rDNA containing the preselected region or to the ribosomal RNA produced by the genes containing the preselected region in the rRNA genes;

preparing rRNA from a sample suspected of containing a species of Alexandrium;

contacting under hybridization conditions the composition containing the labelled nucleotide probe with the rRNA obtained from the sample; and detecting the presence of hybridized labelled probes indicative of the presence of the particular species of Alexandrium.

7. A composition consisting essentially of an isolated oligonucleotide consisting of a nucleotide sequence selected from the group consisting of:

CAUUGGAAUGCAAAGUGGGU (SEQ. ID. NO. 1)
UGGUGGGAGUGUUGCACU (SEQ. ID. NO. 2)
AUGAUAAGUCUCCUGUGG (SEQ. ID. NO. 3)
AUCUGUULKIUGUUCCAUGUG (SEQ. ID. NO. 4)
GCUGCAAGUGCAAUAAUU (SEQ. ID. NO. 5)
ACCCACTTTGCATTCCAATG (SEQ. ID. NO. 6)
AGTGCAACACTCCCACCA (SEQ. ID. NO. 7)
CCACAGGAGACTTATCAT (SEQ. ID. NO. 8)
CACATGGAACAAAAAGACAT (SEQ. ID. NO. 9) and
AATTATTGCACTTGCAGC (SEQ. ID. NO. 10).

8. A composition consisting essentially of an oligonucleotide consisting of a nucleotide sequence selected from the group consisting of SEQ. ID. NOS. 11 through 44.

* * * * *

SEQUENCE LISTING ( 1 ) GENERAL INFORMATION:

( i i i ) NUMBER OF SEQUENCES: 49

-continued ( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

C A U U G G A A U G   C A A A G U G G G U   2 0

( 2 ) INFORMATION FOR SEQ ID NO:2:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

U G G U G G G A G U   G U U G C A C U   1 8

( 2 ) INFORMATION FOR SEQ ID NO:3:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

A U G A U A A G U C   U C C U G U G G   1 8

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA -continued ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:4:

AUCUGUUUUU GUUCCAUGUG 20

( 2 ) INFORMATION FOR SEQ ID NO:5:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

GCUGCAAGUG CAAUAAUU 18

( 2 ) INFORMATION FOR SEQ ID NO:6:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

ACCCACTTTG CATTCCAATG 20

( 2 ) INFORMATION FOR SEQ ID NO:7:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:7:

AGTGCAACAC TCCCACCA 18

( 2 ) INFORMATION FOR SEQ ID NO:8:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:8:

CCACAGGAGA CTTATCAT 18

( 2 ) INFORMATION FOR SEQ ID NO:9:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:9:

CACATGGAAC AAAAAGACAT 20

( 2 ) INFORMATION FOR SEQ ID NO:10:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:10:

AATTATTGCA CTTGCAGC 18

( 2 ) INFORMATION FOR SEQ ID NO:11:

( i ) SEQUENCE CHARACTERISTICS:
( A ) LENGTH: 668 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:11:

```
TAAGTAAGTG GTGGAAATTA AACCAAATAG GATATCTTTA GTAATTGCGA ATGAACAAGG    60
ATATGCTTAG CTTGACAAMT GGAGCTATTG GCTTTGAATT GTATTGTGGA AATGTATTAC   120
CAACAGAGGT GCAGGTGCCA GCCTATTGAA ATAAAGCGTC AATGAGGGTG AGAATCCTGT   180
TTGTCATGTG CARCCCTTTG TGCACGGTGT ATATTTGCTG AGTCACACTC CTTGGCATTG   240
GAATGCAAAG TGGGTGGTAA GTTTCATGTA AAGGTAAACA TGCAAYTGAG ACTGATAGCA   300
CACAAGTRCC ATGAGGGAAA TATGAAAAGG ACTTTGAAAA GAGAATTAAA TGAGTTTGTA   360
TTTGCTGAAC ACAAAGTAAA CAGACTTGAT TTGCTTGGTG GGAGTGTTGC ACTTGCTTGA   420
CAAGAGCTTT GGGCTGTGGG TGTAATGATT CTTTCTTTGC ATGCCAGTTT CTATTTGTAC   480
ATCTGATTAC CTTTGCACAT GAATGATAAG TCTCCTGTGG GGGGTGGATT GCATGTGCAT   540
GTAATGATTT GTGTTTTGAT AMATGTGTCT GGTGTATGTG TGTGTGTTCC TGTGCTTGGG   600
GATGCTTCCT TCCTTGGACT TACAAGCCCT GACACACACA TGCTGGCAAA ATGCTTCTGC   660
TTGACCCG                                                            668
```

( 2 ) INFORMATION FOR SEQ ID NO:12:

( i ) SEQUENCE CHARACTERISTICS:
( A ) LENGTH: 668 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:12:

```
TAAGTAAGTG GTGGAAATTA AACCAAATAG GATATCTTTA GTAATTGCGA ATGAACAAGG    60
ATATGCTTAG CTTGACAAAT GGAGCTATTG GCTTTGAATT GTATTGTGGA AATGTATTAC   120
CAACAGAGGT GCAGGTGCCA GCCTATTGAA ATAAAGCGTC AATGAGGGTG AGAATCCTGT   180
TTGTCATGTG CAGCCCTTTG TGCACGGTGT ATATTTGCTG AGTCACACTC CTTGGCATTG   240
GAATGCAAAG TGGGTGGTAA GTTTCATGTA AAGGTAAACA TGCAAYTGAG ACTGATAGCA   300
CACAAGTRCC ATGAGGGAAA TATGAAAAGG ACTTTGAAAA GAGAATTAAA TGAGTTTGTA   360
TTTGCTGAAC ACAAAGTAAA CAGACTTGAT TTGCTTGGTG GGAGTGTTGC ACTTGCTTGA   420
CAAGAGCTTT GGGCTGTGGR TGTAATGATT CTTTCTTTGC ATGCCAGTTT CTATTTGTAC   480
ATCTGATTAC CTTTGCACAT GAATGATAAG TCTCCTGTGG GGGGTGGATT GCATGTGCAT   540
GTAATGATTT GTGTTTTGAT AMATGTGTCT GGTGTATGTG TGTGTGTTCC TGTGCTTGGG   600
GATGCTTCCT TCCTTGGACT TACAAGCCCT GACACACACA TGCTGGCAAA ATGMTTCTGC   660
TTGACCCG                                                            668
```

( 2 ) INFORMATION FOR SEQ ID NO:13:

( i ) SEQUENCE CHARACTERISTICS:
( A ) LENGTH: 668 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:13:

TAAGTAAGTG GTGGAAATTA AACCAAATAG GATATCTTTA GTAATTGCGA ATGAACAAGG 60

ATATGCTTAG CTTGACAAMY GGAGCTATTG GCTTTGAATT GTATTGTGGA AATGTATTAC 120

CAACAGAGGT GCAGGTGCCA GCCTATTGAA ATAAAGCGTC AATGAGGGTG AGAATCCTGT 180

TTGTCATGTG CAGCCCTTTG TGCACGGTGT ATATTTGCTG AGTCACACTC CTTGGCATTG 240

GAATGCAAAG TGGGTRGTAA GTTTCATGTA AAGGTAAACA TGCAAYTGAG ACTGATAGCA 300

CACAAGTRCC ATGAGGGAAA TATGAAAAGG ACTTTGAAAA GAGAATTAAA TGAGTTTGTA 360

TTTGCTGAAC ACAAAGTAAA CAGACTTGAT TTGCTTGGTG GGAGTGTTGC ACTTGCTTGA 420

CAAGAGCTTT GGGCTGTGGG TGTAATGATT CTTTCTTTGC ATGCCAGTTT CTATTTGTAC 480

ATCTGATTAC CTTTGCACAT GAATGATAAG TCTCCTGTGG GGGGTGGATT GCATGTGCAT 540

GTAATGATTT GTGTTTTGAT AMATGTGYCT GGTGTATGTG TGTGTGTTCC TGTGCTTGGG 600

GATGCTTCCT TCCTTGGACT TACAAGCCCT GACACACACA YGCTGGCAAA ATGCTTCTGC 660

TTGACCCG 668

( 2 ) INFORMATION FOR SEQ ID NO:14:

( i ) SEQUENCE CHARACTERISTICS:
( A ) LENGTH: 668 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:14:

TAAGTAAGTG GTGGAAATTA AACCAAATGG GATATCTTTA GTAATTGCGA ATGAACAAGG 60

ATATGCTTAG CTTGACAAAT GGAGCTATTG GCTTTGAATT GTATTGTGGA AATGTATTAC 120

CAACAGAGGT GCAGGTGCCA GCMTATTGAA ATARAGCGTC AATGAGGGTG AGAATCCTGT 180

TTGYCATGTG CAGCCCTTTG TGCACGGTGT ATATTTGCTG AGTCACACTC CTTGGCATTG 240

GAATGCAAAG TGGGTGGTAA GTTTCATGTM AAGGTAAACA TGCAAYTGAG ACTGATAGCA 300

CACAAGTRCC ATGAGGGAAA TATGAAAAGG ACTTTGAAAA GAGAATTAAA TGAGTTTGTA 360

TTTGCTGAAC ACAAAGTAAA CAGACTTGAT TTGCTTGGTG GGAGTGTTGC ACTTGCTTGA 420

-continued

CAAGAGCTTT GGGCTGTGGG TGTAATGATT CTTTCTTTGC ATGCCAGTTT CTATGTGTAC 480

ATCTGATTAC CTTTGCACAT GAATGATAAG TCTCCTGTGG GGGGTGGATT GCATGTGCAT 540

GTAATGATTT GTGTTTTGAT AAATGTGTCT GGTGTATGTG TGTGTGTTCC TGTGCTTGGG 600

GATGCTTCCT TCCTTGGACT TACAAGCCCT GACACACACA TGCTGGCAAA ATGCTTCTGC 660

TTGACCCG 668

( 2 ) INFORMATION FOR SEQ ID NO:15:

( i ) SEQUENCE CHARACTERISTICS:
( A ) LENGTH: 666 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:15:

TAAGTAAGTG GTGGAAATTA AACCAAATGG GATATCTTTA GTAATTGCGA ATGAACAAGG 60

ATATGCTTAG CTTGACAAAT GGAGCTATTG GCTTTGAATT GTATTGTGGA AATGTATTAC 120

CAACAGAGGT GCAGGTGCCA GCCTATTGAA ATAAAGCGTC AATGAGGGTG AGAATCCTGT 180

TTGTCATGTG CAGCCCTTTG TGCACGGTGT ATATTTGCTG AGTCACACTC CTTGGCATTG 240

GAATGCAAAG TGGGTGGTAA GTTTCATGTA AAGGTAAACA TGCAAYTGAG ACTGATAGCA 300

CACAAGTRCC ATGAGGGAAA TATGAAAAGG ACTTTGAAAA GAGAATTAAA TGAGTTTGTA 360

TTTGCTGAAC ACAAAGTAAA CAGACTTGAT TTGCTTGGTG GGAGTGTTGC ACTTGCTTGA 420

CAAGAGCTTT GGGCTGTGGG TGTAATGATT CTTTCTTTGC ATGCCAGTTT CTATGTGTAC 480

ATCTGATTAC CTTTGCACAT GAATGATAAG TCTCCTGTGG GGGGTGGATT GCATGTGCAT 540

GTAATGATKT GTGTTTTGAT AAATGTGTCT GGTGTATGTG TGTGTTCMTG TGCTTGGGGA 600

TGCTTCCTTC CTTGGACTTA CAAGCCCTGA CACACACATG CTGGCAAAAT RMTTMTGCTT 660

GACCCG 666

( 2 ) INFORMATION FOR SEQ ID NO:16:

( i ) SEQUENCE CHARACTERISTICS:
( A ) LENGTH: 666 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:16:

TAAGTAAGTG GTGGAAATTA AACCAAATGG GATATCTTTA GTAATTGCGA ATGAACAAGG 60

ATATGCTTAG CTTGACAAAT GGAGCTATTG GCTTTGAATT GTATTTGTGG AATGTATTAC 120

-continued

```
CAACAGAGGT GCAGGTGCCA GCMTATTGAA ATARAGCGTC AATGAGGGTG AGAATCCTGT    180
TTGYCATGTG CAGCCCTTTG TGCACGGTGT ATATTTGCTG AGTCACACTC CTTGGCATTG    240
GAATGCAAAG TGGGTGGTAA GTTTCATGTM AAGGTAAACA TGCAAYTGAG ACTGATAGCA    300
CACAAGTRCC ATGAGGGAAA TATGAAAAGG ACTTTGAAAA GAGAATTAAA TGAGTTTGTA    360
TTTGCTGAAC ACAAAGTAAA CAGACTTGAT TTGCTTGGTG GGAGTGTTGC ACTTGCTTGA    420
CAAGAGCTTT GGGCTGTGGG TGTAATGATT CTTTCTTTGC ATGCCAGTTT CTATTTGTAC    480
ATCTGATTAC CTTTGCACAT GAATGATAAG TCTCCTGTGG GGGGTGGATT GCATGTGCAT    540
GTAATGATTT GTGTTTTGAT AAATGTGTCT GGTGTATGTG TGTGTTCCTG TGCTTGGGGA    600
TGCTTCCTTC CTTGGACTTA CAAGCCCTGA CACACACATG CTGGCAAAAT GCTTCTGCTT    660
GACCCG                                                               666
```

( 2 ) INFORMATION FOR SEQ ID NO:17:

( i ) SEQUENCE CHARACTERISTICS:
( A ) LENGTH: 666 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:17:

```
TAAGTAAGTG GTGGAAATTA AACCAAATGG GATATCTTTA GTAATTGCGA ATGAACAAGG     60
ATATGCTTAG CTTGACAMAT GGAGCTATTG GCTTTGAATT GTATTTGTGG AATGTATTAC    120
CAACAGAGGT GCAGGTGCCA GCCTATTGAA ATAAAGCGTC AATGAGGGTG AGAATCCTGT    180
TTGTCATGTG CAGCCCTTTG TGCACGGTGT ATATTTGCTG AGTCACACTC CTTGGCATTG    240
GAATGCAAAG TGGGTGGTAA GTTTCATGTM AAGGTAAACA TGCAATTGAG ACTGATAGCA    300
CACAAGTRCC ATGAGGGAAA TATGAAAAGG ACTTTGAAAA GAGAATTAAA TGAGTTTGTA    360
TTTGCTGAAC ACAAAGTAAA CAGACTTGAT TTGCTTGGTG GGAGTGTTGC ACTTGCTTGA    420
CAAGAGCTTT GGGCTGTGGG TGTAATGATT CTTTCTTTGC ATGCCAGTTT CTATTTGTAC    480
ATCTGATTAC CTTTGCACAT GAATGATAAG TCTCCTGTGG GGGGTGGATT GCATGTGCAT    540
GTAATGATTT GTGTTTTGAT AAAKGTGTCT GGTGTATGTG TGTGTTCCTG TGCTTGGGGA    600
TGCTTCCTTC CTTGGACTTA CAAGCCCTGA CACACACATG CTGGCAAAAT GCTTCTGCTT    660
GACCCG                                                               666
```

( 2 ) INFORMATION FOR SEQ ID NO:18:

( i ) SEQUENCE CHARACTERISTICS:
( A ) LENGTH: 666 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO -continued ( v ) FRAGMENT TYPE:

( v i ) ORIGINAL SOURCE:

( x i ) SEQUENCE DESCRIPTION: SEQ ID NO:18:

```
TAAGTAAGTG GTGGAAATTA AACCAAATGG GATATCTTTA GTAATTGCGA ATGAACAAGG    60
ATATGCTTAG CTTGACAAAT GGAGCTATTG GCTTTGAATT GTATTGTGGA AATGTATTAC   120
CAACAGAGGT GCAGGTGCCA GCMTATTGAA RTAAAGCGTC AATGAGGGTG AGAATCCTGT   180
TTGYCATGTG CAGCCCTTTG TGCACGGTGT ATATTTGCTG AGTCACACTC CTTGGCATTG   240
GAATGCAAAG TGGGTGGTAA GTTTCATGTM AAGGTAAACA TGCAAYTGAG ACTGATAGCA   300
CACAAGTRCC ATGAGGGAAA TATGAAAAGG ACTTTGAAAA GAGAATTAAA TGAGTTTGTA   360
TTTGCTGAAC ACAAAGTAAA CAGACTTGAT TTGCTTGGTG GGAGTGTTGC ACTTGCTTGA   420
CAAGAGCTTT GGGCTGTGGG TGTAATGATT CTTTCTTTGC ATGCCAGTTT CTATTTGTAC   480
ATCTGATTAC CTTTGCACAT GAATGATAAG TCTCCTGTGG GGGGTGGATT GCATGTGCAT   540
GTAATGATTT GTGTTTTGAT AAATGTGTCT GGTGTATGTG TGTGTTCMTG TGCTTGGGGA   600
TGCTTCCTTC CTTGGACTTA CAAGCCCTGA CACACACATG CTGGCAAAAT GCTTCTGCTT   660
GACCCG                                                              666
```

( 2 ) INFORMATION FOR SEQ ID NO:19:

( i ) SEQUENCE CHARACTERISTICS:
( A ) LENGTH: 666 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:19:

```
TAAGTAAGTG GTGGAAATTA AACCAAATGG GATATCTTTA GTAATTGCGA ATGAACAAGG    60
ATATGCTTAG CTTGACAAAT GGAGCTATTG GCTTTGAATT GTATTGTGGA AATGTATTAC   120
CAACAGAGGT GCAGGTGCCA GCCTATTGAA ATAAAGCGTC AATGAGGGTG AGAATCCTGT   180
TTGYCATGTG CAGCCCTTTG TGCACGGTGT ATATTTGCTG AGTCACACTC CTTGGCATTG   240
GAATGCAAAG TGGGTGGTAA GTTTCATGTM AAGGTAAACA TGCAATTGAG ACTGATAGCA   300
CACAAGTACC ATGAGGGAAA TATGAAAAGG ACTTTGAAAA GAGAATTAAA TGAGTTTGTA   360
TTTGCTGAAC ACAAAGTAAA CAGACTTGAT TTGCTTGGTG GGAGTGTWGC ACTTGCTTGA   420
CAAGAGCTTT GGGCTGTGGG TGTAATGATT MTTWCTTTGC ATGCCAGTTT CTATTTGTAC   480
ATCTGATTAC CTTTGCACAT GAATGATAAG TCTCCTGTGG GGGGTGGATT GCATGTGCAT   540
GTAATGATTT GTGTTTTGAT AAATGTGTCT GGTGTATGTG TGTGTTCCTG TGCTTGGGGA   600
TGCTTCCTTC CTTGGACTTA CAAGCCCTGA CACACACATG CTGGCAAAAT GCTTCTGCTT   660
GACCCG                                                              666
```

( 2 ) INFORMATION FOR SEQ ID NO:20:

( i ) SEQUENCE CHARACTERISTICS:
( A ) LENGTH: 666 base pairs

-continued ( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:20:

```
TAAGTAAGTG GTGGAAATTA AACCAAATGG GATATCTTTA GTAATTGCGA ATGAACAAGG   60
ATATGCTTAG CTTGACAAAT KGAGCTATTG GCTTTGAATT GTATTGTGGA AATGYATTAC  120
CAACAGAGGT GCAGGTGCCA GCCTATTGAA ATAAAGCGTC AATGAGGGTG AGAATCCTGT  180
TTGTCATGTG CAGCCCTTTG TGCACGGTGT ATATTTGCTG AGTCACACTC CTTGGCATTG  240
GMATGCAAAG TGGGTGGTAA GTTTCATGTA AAGGTAAACA TGCAAYTGAG ACTGATAGCA  300
CACAAGTRCC ATGAGGGAAA TATGAAAAGG ACTTTGAACA TAGAGTTAAC TGACTTTGTA  360
TTTGCTGAAC ACAAAGTAAA CAGACTTGAT TTGCTTGGTG GGAGTGTTGC ACTTGCTTGA  420
CAAGAGCTTT GGGCTGTGGG TGTAATGATT CTTTCTTTGC ATGCCAGTTT CTATTTGTAC  480
ATCTGATTAC CTTTGCACAT GAATGATAAG YCTCCTGTGG GGGRTGGATT GCATGTGCAT  540
GTAATGATTT GTGTTTTGAT AAMTGTGTCT GGTGTATGTG TGTGTTCCTG TGCTWGGGGA  600
TRCKTCCTTC CTTGGACTTA CAAGCCCTGA CACACACATG CTGGCAAAAT GCTTCTGCTT  660
GACCCG                                                             666
```

( 2 ) INFORMATION FOR SEQ ID NO:21:

( i ) SEQUENCE CHARACTERISTICS:
( A ) LENGTH: 666 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:21:

```
TAAGTAAGTG GTGGAAATTA AACCAAATGG GATATCTTTA GTAATTGCGA ATGAACAAGG   60
ATATGCTTAG CTTGACAAAT GGAGCTATTG GCTTTGAATT GTATTGTGGA ARTGYATTAC  120
CAACAGAGGT GCAGGTGCCA GCCTATTGAA ATAAAGCGTC AATGAGGGTG AGAATCCTGT  180
TTGTCATGTG CAGCCCTTTG TGCACGGTGT ATATTTGCTG AGTCACACTC CTTGGCATTG  240
GMATGCAAAG TGGGTGGTAA GTTTCATGTA AAGGTAAACA TGCAAYTGAG ACTGATAGCA  300
CACAAGTRCC ATGAGGGAAA TATGAAAAGG ACTTTGAACA TAGAGTTAAC TGACTTTGTA  360
TTTGCTGAAC ACAAAGTAAA CAGACTTGAT TTGCTTGGTG GGAGTGTTGC ACTTGCTTGA  420
CAAGAGCTTT GGGCTGTGGG TGTAATGATT CTTTCTTTGC ATGCCAGTTT CTATTTGTAC  480
ATCTGATTAC CTTTGCACAT GAATGATAAG TCTCCTGTGG GGGRTGGATT GCATGTGCAT  540
GTAATGATTT GTGTTTTGAT AMATGTGTCT GGTGTATGTG TGTGTTCCTG TGCTTGGGGA  600
```

-continued

TRCKTCCTTC CTTGGACTTA CAAGCCCTGA CACACACATG CTGGCAAAAT GCTTCTGCTT 660

GACCCG 666

( 2 ) INFORMATION FOR SEQ ID NO:22:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:22:

TAAGTAAGTG GTGGAAATTA AACCAAATGG GATTTCTTTA GTAATTGCGA ATGAACAAGG 60

ATATGCTTAG CTTGACAAAT GGAGCTTTTG GCTTTGAGTT GTATTGTGGA AATGTACCAC 120

CAACAGAGGT GCAAGTGYCA GCCATTTGAA AGAAAGCGTC AATGAGGGTG AGAATCCTGT 180

TTGTCATGTG CAGCCCTCTG TGCACGGTGT ATATTTGCTG AGTCACACTC CTTGGCATTG 240

GAATGCAAAG TGGGTGGTAA GTTTCATACA AAGGTAAATA TGCAATTGAG ACTGATAGCA 300

CACAAGTACC ATGAGGGAAA TATGAAAAGG ACTTTGAAAA GAGAATTAAA TGAGTTTGTA 360

TTTGCTGAAC ACAAAGCAAA CAGACTTGAT TTGCTTGGTG AGATTGTAGT GCTTGCTTGA 420

CAATAGGTTT TGGCTGTGGG TGAAATGATT CTTTCTTTGC ATGCCAGGTT CTATGTGTAC 480

ATTTGATTAC CTTTGCACAT GAATGGYAAT TTTCCTGCGG GGGGTGGATT GCATGTGCAT 540

GTAATGATTT GTGTTTTGAT GAATGTGTCT GGTGTATCTG TTTTTGTTCC ATGTGTTTGA 600

GGTTGCTTCC TTCCTTGGGC TTACAAGCCC TGACACACAC AATCTGGCAA AATGTTTCTG 660

CTTGACCCG 669

( 2 ) INFORMATION FOR SEQ ID NO:23:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:23:

TAAGTAAGTG GTGGAAATTA AACCAAATGG GATTTCTTTA GTAATTGCGA ATGAACAAGG 60

ATATGCTTAG CTTGACAAAT GGAGCTTTTG GCTTTGAGTT GTATTGTGGA AATGTACCAC 120

CAACAGAGGT GCAAGTGTCA GCCATTTGAA AGAAAGCGYC AATGAGGGTG AGAATCCTGT 180

TTGTCATGTG CAGCCCTCTG TGCACGGTGT ATATTTGCTG AGTCACACTC CTTGGCATTG 240

GAATGCAAAG TGGGTGGTAA GTTTCATACA AAGGTAAATA TGCAATTGAG ACTGATAGCA 300

-continued

```
CACAAGTACC ATGAGGGAAA TATGAAAAGG ACTTTGAAAA GAGAATTAAA TGAGTTTGTA 360
TTTGCTGAAC ACAAAGCAAA CAGACTTGAT TTGCTTRGTG AGATTGTAGT GCTTGCTTGA 420
CAATAGGTTT TGGCTGTGGG TGAAATGATT CTTTCTTTGC ATGCCAGGTT CTATGTGTAC 480
ATTTGATTAC CTTTGCACAT GAATGGTAAT TTTCCTGCGG GGGGTGGATT GCATGTGCAT 540
GTAATGATTT GTGTTTTGAT GAATGTGTCT GGTGTATCTG TTTTTGTTCC ATGTGTTTGA 600
GGTTGCTTCC TTCCTTGGGC TTACAAGCCC TGACACACAC AATCTGGCAA AATGTTTCTG 660
CTTGACCCG 669
```

( 2 ) INFORMATION FOR SEQ ID NO:24:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:24:

```
TAAGTAAGTG GTGGAAATTA AACCAAATGG GATTTCTTTA GTAATTGCGA ATGAACAAGG 60
ATATGCTTAG CTTGACAAAT GGAGCTTTTG GCTTTGAGTT GTATTGTGGA AATGTACCAC 120
CAACAGAGGT GCAAGTGTCA GCCATTTGAA AGAAAGCGTC AATGAGGGTG AGAATCCTGT 180
TTGTCATGTG CAGCCCTCTG TGCACGGTGT ATATTTGCTG AGTCACACTC CTTGGCATTG 240
GAATGCAAAG TGGGTGGTAA GTTTCATACA AAGGTAAATA TGCAATTGAG ACTGATAGCA 300
CACAAGTACC ATGAGGGAAA TATGAAAAGG ACTTTGAAAA GAGAATTAAA TGAGTTTGTA 360
TTTGCTGAAC ACAAAGCAAA CAGACTTGAT TTGCTTGGTG AGATTGTAGT GCTTGCTTGA 420
CAATAGGTTT TGGCTGTGGG TGAAATGATT CTTTCTTTGC ATGCCAGGTY CTATGTGTAC 480
ATTTGATTAC CTTTGCACAT RAATGGTART YTTCCTGCGG GGGGTGGATT GCATGTGCAT 540
GTAATGATTT GTGTTTTGAT GAATGTGTCT GGTGTATCTG TTTTTGTTCC ATGTGTTTGA 600
GGTTGCTTCC TTCCTTGGGC TTACAAGCCC TGACACACAC AATCTGGCAA AATGTTTCTG 660
CTTGACCCG 669
```

( 2 ) INFORMATION FOR SEQ ID NO:25:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:25:

-continued

```
TAAGTAAGTG GTGGAAATTA AACCAAATGG GATTTCTTTA GTAATTGCGA ATGAACAAGG    60
ATATGCTTAG CTTGACAAAT GGAGCTTTTG GCTTTGAGTT GTATTGTGGA AATGTACCAC   120
CAACAGAGGT GCAAGTGTCA GCCATTTGAA AGAAAGCGTC AATGAGGGTG AGAATCCTGT   180
TTGTCATGTG CAGCCCTCTG TGCACGGTGT ATATTTGCTG AGTCACACTC CTTGGCATTG   240
GAATGCAAAG TGGGTGGTAA GTTTCATACA AAGGTAAATA TGCAATTGAG ACTGATAGCA   300
CACAAGTACC ATGAGGGAAA TATGAAAAGG ACTTTGAAAA GAGAATTAAA TGAGTTTGTA   360
TTTGCTGAAC ACAAAGCAAA CAGACTTGAT TTGCTTGGTG AGATTGTAGT GCTTGCTTGA   420
CAATAGGTTT TGGCTGTGGG TGAAATGATT CTTTCTTTGC ATGCCAGGTT CTATGTGTAC   480
ATTTGATTAC CTTTGCACAT GAATGGTAAT TTTCCTGCGR GGGGTGGATT GCATGTGCAT   540
GTAATGATTT GTGTTTTGAT GAATGTGTCT GGTGTATCTG TTTTTGTTCC ATGTGTTTGA   600
GGTTGCTTCC TTCCTTGGGC TTACAAGCCC TGACACACAC AATCTGGCAA AATGTTTCTG   660
CTTGACCCG                                                           669
```

( 2 ) INFORMATION FOR SEQ ID NO:26:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:26:

```
TAAGTAAGTG GTGGAAATTA AACCAACTGG GATCTCTTCA GTAATTGCGC ATGAACCAGG    60
ATATGCTTAG CTTGACAAAT GGAGCTGCTG GCTCTGAATT GTATTGTGGG AATGTATTAC   120
CAACAGAGGT GCAGGTGTCA GCCATTTGAA AGAAAGCATC AATGAGGGTG AGAGTCCTGT   180
TTGTCATGTG CAGCCTTCTG TGCACGGTGT ATATTTGCTG AGTCACACTC CTYGGCATTG   240
GAATGCAAAG TGGGTGGTAA GTTTCATGCA AAGGTAAATA TGCAATTGAG ACTGATAGCG   300
CACAAGTACC ATGAGGGACA TATGAAAAGG ACTTTGAACA GAGAATTAAA TGAGTTTGTA   360
TTTGCTAAAC ACAAAGTAAA CAGACTTGAT TTCCTCAGTG AGATTGTAGT GMTTGCTTRA   420
CAATGGGTTT TGGCTGCAAG TGCAATAATT CTTGCTTTGT GTGCCAGTTT TTATGTGGAC   480
ATTTGATTAC CTTTGCACAT GAATGGTAAT TTTCCTGCGG GGTGTGGATT GCATATGCAT   540
GTAATGATTT GCATGTTYGT TAARTGTGTC TGGTGTATTT GTTTGTGTCC TTGTCCTTGA   600
GGTTGCTTTC TCCCTTGGGC TTACATGCCC TGGCACACAC ATTCTGGCAA AATGCTTCTG   660
CTTGACCCG                                                           669
```

( 2 ) INFORMATION FOR SEQ ID NO:27:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:27:

```
TAAGTAAGTG GTGGAAATTA AACCAACTGG GATCTCTTCA GTAATTGCGC ATGAACCAGG    60
ATATGCTTAG CTTGACAAAT GGAGCTGCTG GCTCTGAATT GTATTGTGGG AATGTATTAC   120
CAACAGAGGT GCAGGTGTCA GCCATTTGAA AGAAAGCATC AATGAGGGTG AGAGTCCTGY   180
TTGTCATGTG CAGCCTTCTG TGCACGGTGT ATATTTGCTG AGTCACACTC CTYGGCATTG   240
GAATGCAAAG TGGGTGGTAA GTTTCATGCA AAGGTAAATA TGCAATTGAG ACTGATAGCR   300
CACAAGTACC ATGAGGGACA TATGAAAAGG ACTTTGAACA GAGAATTAAA TGAGTTTGTA   360
TTTGCTAAAC ACAAAGTAAA CAGACTTGAT TTCCTCAGTG AGATTGTAGT GCTTGCTTRA   420
CAATGGGTTT TGGCTGCAAG TGCAATAATT CTTGCTTTGT GTGCCAGTTT TTATGTGGAC   480
ATTTGATTAC CTTTGCACAT GAATGGYAAT TTTCCTGCCG GGTGTGGATT GCATATGCAT   540
GTAATGATTT GCATGTTTGT TAAATGTGTC TGGTGTATTT GTTTGTGTCC TTGTCCTTGA   600
GGTTGCTTTC TCCCTTGGGC TTACATGCCC TGGCACACAC ATTCTGGCAA AATGCTTCTG   660
CTTGACCCG                                                           669
```

( 2 ) INFORMATION FOR SEQ ID NO:28:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:28:

```
TAAGTAAGTG GTGGAAATTA AACCAACTGG GATCTCTTCA GTAATTGCGC ATGAACCAGG    60
ATATGCTTAG CTTGACAAAT GGAGCTGCTG GCTCTGAATT GTATTGTGGG AATGTATTAC   120
CAACAGAGGT GCAGGTGTCA GCCATTTGAA AGAAAGCATC AATGAGGGTG AGAGTCCTGT   180
TTGTCATGTG CAGCCTTCTG TGCACGGTGT ATATTTGCTG AGTCACACTC CTTGGCATTG   240
GAATGCAAAG TGGGTGGTAA GTTTCATGCA AAGGTAAATA TGCAATTGAG ACTGATAGCG   300
CACAAGTACC ATGAGGGACA TATGAAAAGG ACTTTGAACA GAGAATTAAA TGAGTTTGTA   360
TTTGCTAAAC ACAAAGTAAA CAGACTTGAT TTCCTCAGTG AGATTGTAGT GMTTGCTTRA   420
CAATGGGTTT KGGCTGCAAG TGCAATAATT CTTGCTTTGT GTGCCAGTTT TTATGTGGAC   480
ATTTGATTAC CTTTGCACAT GAATGGTAAT TTTCCTGCGG GGTGTGGATT GCATATGCAT   540
GTAATGATTT GCATGTTTGT TAAATGTGTC TGGTGTATTT GTTTGTGTCC TTGTCCTTGA   600
GGTTGCTTTC TCCCTTGGGC TYACATGCCC TGGCACACAC ATTCTGGCAA AATGCTTCTG   660
CTTGACCCG                                                           669
```

-continued ( 2 ) INFORMATION FOR SEQ ID NO:29:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:29:

TAAGTAAGTG GTGGAAATTA AACCAACTGG GATCTCTTCA GYAATTGCGC ATGAACCAGG 60

ATATGCTTAG CTTGACAAAT GGAGCTGCTG GCTCTGAATT GTATTGTGGG AATGTATTAC 120

CAACAGAGGT GCAGGTGTCA GCCATTTGAA AGAAAGCATC AATGAGGGTG AGAGTCCTGT 180

TTGTCATGTG CAGCCTTCTG TGCACGGTGT ATATTTGCTG AGTCACACTC CTTGGCATTG 240

GAATGCAAAG TGGGTGGTAA GTTTCATGCA AAGGTAAATA TGCAATTGAG ACTGATAGCG 300

CACAAGTACC ATGAGGGACA TATGAAAAGG ACTTTGAACA GAGAATTAAA TGAGTTTGTA 360

TTTGCTAAAC ACAAAGTAAA CAGACTTGAT TTCCTCARTG AGATTGTAGT GCTTGCTTRA 420

CAATGGGTTT TGGCTGCAAG TGCAATAATT CTTGCTTTGT GTGCCAGTTT TTATGTGGAC 480

ATTTGATTAC CTTTGCACAT GAATGGTAAT TTTCCTGCGG GGTGTGGATT GCATATGCAT 540

GTAATGATTT GCATRTKTGT TAAATGTGTC TGGTGTATTT GTTTGTGTCC TTGTCCTTGA 600

GGTTGCTTTC TCCCTTGGGC TTACATGCCC TGGCACACAC ATTCTGGCAA RATGCTTCTG 660

CTTGACCCG 669

( 2 ) INFORMATION FOR SEQ ID NO:30:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:30:

TAAGTAAGTG GTGGAAATTA AACCAACTGG GATCTCTTCA GTAATTGCGC ATGAACCAGG 60

ATATGCTTAG CTTGACAAAT GGAGCTGCTG GCTCTGAATT GTATTGTGGG AATGTATTAC 120

CAACAGAGGT GCAGGTGTCA GCCATTTGAA AGAAAGCATC AATGAGGGTG AGAGTCCTGT 180

TTGTCATGTG CAGCCTTCTG TGCACGGTGT ATATTTGCTG AGTCACACTC CTTGGCATTG 240

GAATGCAAAG TGGGTGGTAA GTTTCATGCA AAGGTAAATA TGCAATTGAG ACTGATAGCG 300

CACAAGTACC ATGAGGGACA TATGAAAAGG ACTTTGAACA GAGAATTAAA TGAGTTTGTA 360

TTTGCTAAAC ACAAAGTAAA CAGACTTGAT TTCCTCAGTG AGATTGTAGT GCTTGCTTAA 420

-continued

```
CAATGGGTTT TGGCTGCAAG TGCAATAATT CTTGCTTTGT GTGCCAGTTT TTATGWGGAC   480
ATTTGATTAC CTTTGCACAT GAATGGTAAT TTTCCTGCGG GGTGWGGATT GCATATGCAT   540
GTAATGAWTT GCATGTTTGT TAAATGTGTC TGGTGTATTT GYTTGTGTCC TTGTCCTTGA   600
GGTTGCTTTC TCCCTTGGGC TTACATGCCC TGGCACACAC ATTCTGGCAA AATGCTTCTG   660
CTTGACCCG                                                           669
```

( 2 ) INFORMATION FOR SEQ ID NO:31:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:31:

```
TAAGTAAGTG GTGGAAATTA AACCAACTGG GATCTCTTCA GTAATTGCGC ATGAACCAGG    60
ATATGCTTAG CTTGACAAAT GGAGCTGCTG GCTCTGAATT GTATTGTGGG AATGTATTAC   120
CAACAGAGGT GCAGGTGTCA GCCATTTGAA AGAAAGCATC AATGAGGGTG AGAGTCCTGT   180
TTGTCATGTG CAGCCTTCTG TGCACGGTGT ATATTTGCTG AGTCACACTC CTYGGCATTG   240
GAATGCAAAG TGGGTGGTAA GTTTCATGCA AAGGTAAMTA TGCAATTGAG ACTGATAGCG   300
CACAAGTACC ATGAGGGACA TATGAAAAGG ACTTTGAACA GAGAATTAAA TGAGTTTGTA   360
TTTGCTAAAC ACAAAGTAAA CAGACTTGAT TTCCTCAGTG AGATTGTAGT GCTTGCTTRA   420
CAATGGGTTT TGGCTGCAAG TGCAATAATT CTTGCTTTGT GTGCCAGTTT TTATGTGGAC   480
ATTTGATTAC CTTTGCACAT GAATGGTAAT TTTCCTGCGG GGTGTGGATT GCATATGCAT   540
GTAATGATTT GCATGTTTGT TAAATGTGTC TGGTGTATTT GTTTGTGTCC TTGTCCTTGA   600
GGTTGCTTTC TCCCTTGGGC TTACATGCCC TGGCACACAC ATTCTGGCAA AATGCTTCTG   660
CTTGACCCG                                                           669
```

( 2 ) INFORMATION FOR SEQ ID NO:32:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:32:

```
TAAGTAAGTG GTGGAAATTA AACCAACTGG GATCTCTTCA GTAATTGCGC ATGAACCAGG    60
ATATGCTTAG CTTGACAAAT GGAGCTGCTG GCTCTGAATT GTATTGTGGG AATGTATTAC   120
```

-continued

```
CAACAGAGGT GCAGGTGTCA GCCATTTGAA AGAAAGCATC AATGAGGGTG AGAGTCCTGT 180
TTGTCATGTG CAGCCTTCTG TGCACGGTGT ATATTTGCTG AGTCACACTC CTYGGCATTG 240
GAATGCAAAG TGGGTGGTAA GTTTCATGCA AAGGTAAATA TGCAATTGAG ACTGATAGCG 300
CACAAGTACC ATGAGGGACA TATGAAAAGG ACTTTGAACA GAGAATTAAA TGAGTTTGTA 360
TTTGCTAAAC ACAAAGTAAA CAGACTTGAT TTCCTCAGTG AGATTGTAGT GMTTGCTTRA 420
CAATGGGTTT TGGCTGCAAG TGCAATAATT CTTGCTTTGT GTGCCAGTTT TTATGTGGAC 480
ATTTGATTAC CTTTGCACAT GAATGGTAAT TTTCCTGCGG GGTGTGGATT GCATATGCAT 540
GTAATGATTT GCATGTTTGT TAAATGTGTC TGGTGTATTT GTTTGTGTCC TTGTCCTTGA 600
GGTTGCTTTC TCCCTTGGGC TTACATGCCC TGGCACACAC ATTCTGGCAA AATGCTTCTG 660
CTTGACCCG                                                         669
```

( 2 ) INFORMATION FOR SEQ ID NO:33:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:33:

```
TAAGTAAGTG GTGGAAATTA AACCAACTGG GATCTCTTCA GTAATTGCGC ATGAACCAGG  60
ATATGCTTAG CTTGACAAAT GGAGCTGCTG GCTCTGAATT GTATTGTGGG AATGTATTAC 120
CAACAGAGGT GCAGGTGTCA GCCATTTGAA AGAAAGCATC AATGAGGGTG AGAGTCCTGT 180
TTGTCATGTG CAGCCTTCTG TGCACGGTGT ATATTTGCTG AGTCACACTC CTYGGCATTG 240
GAATGCAAAG TGGGTGGTAA GTTTCATGCA AAGGTAAATA TGCAATTGAG ACTGATAGCG 300
CACAAGTACC ATGAGGGACA TATGAAAAGG ACTTTGAACA GAGAATTAAA TGAGTTYGTA 360
TTTGCTAAAC ACAAAGTAAA CAGACTTGAT TTCCTCAGTG AGATTGTAGT GCTTGCTTRA 420
CAATGGGTTT TGGCTGCAAG TGCAATAATT CTTGCTTTGT GTGCCAGTTT TTATGTGGAC 480
ATTTGATTAC CTTTGCACAT GAATGGTAAT TTTCCTGCGG GGTGTGGATT GCATATGCAT 540
GTAATGATTT GCATGTTTGT TAAATGTGTC TGGTGTATTT GTTTGTGTCC TTGTCCTTGA 600
GGTTGCTTTC TCCCTTGGGC TTACATGCCC TGGCACACAC ATTCTGGCAA AATGCTTCTG 660
CTTGACCCG                                                         669
```

( 2 ) INFORMATION FOR SEQ ID NO:34:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO -continued ( v ) FRAGMENT TYPE:

( v i ) ORIGINAL SOURCE:

( x i ) SEQUENCE DESCRIPTION: SEQ ID NO:34:

TAAGTAAGTG GTGGAAATTA AACCAACTGG GATCTCTTTA GTAATTGCGC ATGAACCAGG 60

ATATGCTTAG CTTGACAAAT GGAGCTGCTG GCTCTGAATT GTATTGTGGG AATGTATTAC 120

CAACAGAGGT GCAGGTGTCA GCCATTTGAA AGAAAGCATC AATGAGGGTG AGAGTCCTGT 180

TTGTCATGTG CAGCCTTCTG TGCACGGTGT ATATTTGCTG AGTCACACTC CTTGGCATTG 240

GAATGCAAAG TGGGTGGTAA GTTTCATGCA AAGGTAAATA TGCAATTGAG ACTGATAGCG 300

CACAAGTACC ATGAGGGACA TATGAAAAGG ACTTTGAAMA GAGAATTAAA TGAGTTTGTA 360

TTTGCTAAAC ACAAAGTAAA CAGACTTGAT TTCCTCAGTG AGATTGTAGT GMTTGCTTRA 420

CAATGGGTWT TGGCTGCAAG TGCAATAATT MTTGCTTTGT GTRCCMGTTT TTATGTGGAC 480

ATTTGRTTAC CTTKGCACAT GAATGGTAAT TTTCCTGCGG GGTGTGGATT GCATATGCAT 540

GWAATGATTT GCATGTTTGT TAAATGTGTC TGGTGTATTT GTTTGTGTCC TTGTCCTTGA 600

GGTTGCTTTC TCCCTTGGGC TTACATGCCC TGGCACACAC ATTCTGGCAA AATRCTTCTR 660

CTTGACCCG 669

( 2 ) INFORMATION FOR SEQ ID NO:35:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:35:

TAAGTAAGTG GTGGAAATTA AACCAACTGG GATCTCTTTA GTAATTGCGC ATGAACCAGG 60

ATATGCTTAG CTTGACAAAT GGAGCTGCTG GCTCTGAATT GTATTGTGGG AATGTATTAC 120

CAACAGAGGT GCAGGTGTCA GCCATTTGAA AGAAAGCATC AATGAGGGTG AGAGTCCTGT 180

TTGTCATGTG CAGCCTTCTG TGCACGGTGT ATATTTGCTG AGTCACACTC CTTGGCATTG 240

GAATGCAAAG TGGGTGGTAA GTTTCATGCA AAGGTAAATA TGCAATTGAG ACTGATAGCG 300

CACAAGTACC ATGAGGGACA TATGAAAAGG ACTTTGAACA GAGAATTAAA TGAGTTTGTA 360

TTTGCTAAAC ACAAAGTAAA CAGACTTGAT TTCCTCAGTG AGATTGTAGT GCTTGCTTRA 420

CAATGGGTTT TGGCTGCAAG TGCAATAATT CTTGCTTTGT GTGCCMGTTT TTATGTGGAC 480

ATTTGATTAC CTTKGCACAT GAATGGTAAT TCTCCTGCGG GGTGTGGATT GCATWTGCAT 540

GTAATGATTT GCATGTTTGT TAAATGTGTC TGGTGTATTT GTTTGTGTCC TTGTCCTTGA 600

GGTTGCTTTC TCCCTTGGGC TTACATGCCC TGGCACACAC ATTCTGGCAA AATGCTTCTG 660

CTTGACCCG 669

( 2 ) INFORMATION FOR SEQ ID NO:36:

( i ) SEQUENCE CHARACTERISTICS:
( A ) LENGTH: 669 base pairs

-continued ( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:36:

TAAGTAAGTG GTGGAAATTA AACCAACTGG GATCTCTTTA GTAATTGCGC ATGAACCAGG 60

ATATGCTTAG CTTGACAAAT GGAGCTGCTG GCTTTGAATT GTATTGTGGA AAYGTATTAC 120

CAACAGAGGT GCAGGTGCCA GCCATTTGAA AGAAAGCGTC AATGAGGGTG AGAATCCTGT 180

TTGTCATATG CAGCCCTCTG TGCACGGTGT ATATTTGCTG AGTCACACTC CTTGGCATTG 240

GAATGCAAAG TGGGTGGTAA GTTTCATGCA AAGGTAAATA TGCAATTGAG ACTGATAGCG 300

CACAAGTACC ATGAGGGACA TATGAAAAGG ACTTTGAAAA GAGAATTAAA CGAGTTTGTA 360

TTTGCTGAAC ACAAAGTAAA CAGATGTGAT TTCCTTAGTG AGATTGTAGC ACTTGCTTGA 420

CAATAGGTTT TGGCGGTGGG TGCAATGATT CTTGCTTTGT ATGCCAGTTT CTATGTGGAC 480

ATTTGATTAC CTGTGCACTT GAATGGTAAT TTTCCTGCGG GGGGTGGATT GCATATGCAT 540

GTAATTATTT GCATGTTTTA TTACTGTGTC TGGTGTATGT GTTTGTGTCM TTGTGCTTGT 600

GGTTGCTTTC TTCCTTGGGC TTGCAAGCCC TGGCACACAC ATTCTGGCAA CATGCTTCTG 660

CTTGACCCG 669

( 2 ) INFORMATION FOR SEQ ID NO:37:

( i ) SEQUENCE CHARACTERISTICS:
( A ) LENGTH: 666 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:37:

TAAGTAAGTG GTGGAAATTA AACCAAATGG GATTCCTTTA GTAATTGCGA ATGAACAAGG 60

ATATGCTTAG CTTGATAATT GGGGCTTCTG GCTTTGAAYT GTGTTTTTGA AATGTATTAC 120

CAACAGAGGT GCAGGTGTTA GCATATTGGA AGAAAGCGTC AATGAGGGTG AGAATCCTTT 180

TTGTCATGTG CAGTCCTCTG TGCACGGTGT ATGTTTGCTG AGTCACACTC CTTGGCATTG 240

GAATGCAAAG TGGGTGGTAA GTTTCATGTA AAGGTAAATA TATGATTGAG ACTGATAGTG 300

CACAAGTACC ATGAGGGAAA TATGAAAAGG ACTTTGAAAA GAGAATTAAA TGAGTTTGTA 360

TTTGCTGAAC AGAAAGTAAA CAGATTTGAT TTTGCTGGGT GAGATTGTGG TGCTTGCTTG 420

ACACTTATGT GGTTGTAAGT ACAATGATTC TTACTTTGTG TGCCAGTTTT TTGCACATTT 480

GAACATTCTT GCGTATGAAT GGTAATATTC CTGYGGGGGT TGGATTGCAT ACGTATGTAA 540

GCATTTGTGT TCTGAACTAT GTGTTTGGTG ACTTTGTTTG TACGCTATGT GTACAGAAGG 600

TTGTTTTCTT CCTGGGTCAA CAAGCCTTAA CACAGACTTG CTGGCAAAAT GCTTCTGCTT 660

GACCCG 666

( 2 ) INFORMATION FOR SEQ ID NO:38:

( i ) SEQUENCE CHARACTERISTICS:
( A ) LENGTH: 671 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:38:

TAAGTAAGTG GTGGAAATTA AACCAAATGG GATTCCTTAA GTAATTGCGA ATGAACAAGG 60

ACATGCTTAG CTTGACAATT GGAGCCTCTG GCTTCGACTT GTATTTTTGA AATGTATTAC 120

CAACAGAGGT GCAGGTGTCA GCCTATTGAA AGAAAGCGTC AATGAGGGTG AGAATCCTGT 180

TTGTCATGTG CAATCCTCTG TGCACGGTGT ATGTTTGCTG AGTCACACTC CTTGGCATTG 240

GAATGCAAAG TGGGTGGTAA GTTTCATGTA AAGGTAAATA TAGGATTGAG ACTGATAGCA 300

CACAAGTRCC ATGAGGGAAA TATGAAAAGG ACTTTGAAAA GAGAATTAAA TGAGTTTGTA 360

TTTGCTGAAC AGAAAATAAA CAGATTTGAT GTTGCTTGGT GAGATTGTGG TGCTTGCTTG 420

ACAATAGGTT TTGATTGTGG GTGCGATGAT TCTTGCTTTG CTTGCCAGTT TCTATTTGTA 480

CATTTGATTA CCCTTGCACA TGAATGGTAA TTTTCCTGCG GGGTTTGGAT TGCATGTGTT 540

TGTGATGATT TGTGTTTTGA TTCATGTGTC TGGTGCTTTT GTAATTGCTC ATTTCTTGAA 600

GCTGGGCCTA CCCTACTAGA GCTTACAAGC CCTGGCACAC AATTGCTGGC AAAATGCTTC 660

TGCTTGACCC G 671

( 2 ) INFORMATION FOR SEQ ID NO:39:

( i ) SEQUENCE CHARACTERISTICS:
( A ) LENGTH: 671 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:39:

TAAGTAAGTG GTGGAAATTA AACCAAATGG GATTCCTTAA GTAATTGCGA ATGAACAAGG 60

ACATGCTTAG CTTGACAATT GGAGCCTCTG GCTTCGACTT GTATTTTTGA AATGTATTAC 120

CAACAGAGGT GCAGGTGTCA GCCTATTGAA AGAAAGCGTC AATGAGGGTG AGAATCCTGT 180

TTGTCATGTG CAATCCTCTG TGCACGGTGT ATGTTTGCTG AGTCACACTC CTTGGCATTG 240

GAATGCAAAG TGGGTGGTAA GTTTCATGTA AAGGTAAATA TAGGATTGAG ACTGATAGCA 300

-continued

CACAAGTACC ATGAGGGAAA TATGAAAAGG ACTTTGAAAA GAGAATTAAA TGAGTTTGTA 360

TTTGCTGAAC AGAAAATAAA CAGATTTGAT GTTGCTTGGT GAGATTGTGG TGCTTGCTTG 420

ACAATAGGTT TTGATTGTGG GTGCGATGAT TCTTGCTTTG CTTGCCAGTT TCTATTTGTA 480

CATTTGATTA CCCTTGCACA TGAATGGTAA TTTTCCTGCG GGGTTTGGAT TGCATGTGTT 540

TGTGATGATT TGTGTTTTGA TGCATGTGTC TGGTGCTTTT GTAATTGCTC ATTTCTTGAA 600

GCTGGGCCTA CCCTACTAGA GCTTACAAGC CCTGGCACAC AATTGCTGGC AAAATGCTTC 660

TGCTTGACCC G 671

( 2 ) INFORMATION FOR SEQ ID NO:40:

( i ) SEQUENCE CHARACTERISTICS:
( A ) LENGTH: 671 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:40:

TAAGTAAGTG GTGGAAATTA AACCAAATGG GATTCCTTAA GTAATTGCGA ATGAACAAGG 60

ACATGCTTAG CTTGACAATT GGAGCCTCTG GCTTCGACTT GTATTTTTGA AATGTATTAC 120

CAACAGAGGT GCAGGTGTCA GCCTATTGAA AGAAAGCGTC AATGAGGGTG AGAATCCTGT 180

TTGTCATGTG CAATCCTCTR TGCACGGTGT ATGTTTGCTG AGTCACACTC CTTGGCATTG 240

GAATGCAAAG TGGGTGGTAA GTTTCATGTA AAGGTAAATA TAGGATTGAG ACTGATAGCA 300

CACAAGTACC ATGAGGGAAA TATGAAAAGG ACTTTGAAAA GAGAATTAAA TGAGTTTGTA 360

TTTGCTGAAC AGAAAATAAA CAGATTTGAT GTTGCTTGGT GAGATTGTGG TGCTTGCTTG 420

ACAATAGGTT TTGATTGTGG GTGCGATGAT TCTTGCTTTG CTTGCCAGTT TCTATTTGTA 480

CATTTGATTA CCCTTGCACA TGAATGGTAA TTTTCCTGCG GGGTTTGGAT TGCATGTGTT 540

TGTGATGATT TGTGTTTTGA TGCATGTGTC TGGTGCTTTT GTAATTGCTC ATTTCTTGAA 600

GCTGGGCCTA CCCTACTAGA GCTTACAAGC CCTGGCACAC AATTGCTGGC AAAATGCTTC 660

TGCTTGACCC G 671

( 2 ) INFORMATION FOR SEQ ID NO:41:

( i ) SEQUENCE CHARACTERISTICS:
( A ) LENGTH: 676 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:41:

```
TAAGTAGGCG GTGGAAAATG AACCAAATGG GATTCCTTAA GTAATTGCGA ATGAACAAGG    60
AAATGCTCAG CTTGAAAAAT GGGGCCTTTG GCTTTGAATT GTAATTTTGA AATGTATTGC   120
CAATGGAGGC GCAGGTGCAA GCCTATTGAA AGAAAGCGTC AATGAGGGTG AGATTCCTTT   180
TTGTCATTTG CAGTCCTCCG TGCACGGTAT ATATTTGACG AGTCACACTC CTCGGCATTG   240
GAATGCAAAG TGGGTGGTAA ATTCCATGTA AAGGTAAATA TATTATTGAG ACTGATAGCA   300
AACAAGTACC ATGAGGGAAA TATGAAAAGG ACTTTGAAAA GAGAATTAAA AGAGTCTGCA   360
TTTGCTGAAC AGAAAGCAAA CAGAATTGAT TTTACTTGGT GAGATTGTTG TGCTTACTCT   420
ATCATTTATA TGGTTGATGT GGGTGCGATG GTTCTTACCT TGAATGTCAG CTTCTATTTC   480
TGCAAATCAT TACCCTTGCA CATGAATGGT AACTTGCCTG CGGGTATTGG AATGCATGTG   540
TTTGCAATGA TTTGTGATTT GACGCATGTG TTTGGTGAAA TTTGTATATG CTCTTTTGTC   600
GAAGGGGAAA GCTTACTTTT TTGAGCATTG CAAGCCCTTA CACATCAGTG CTGGCAAAAT   660
GTTTCTGCTT GACCCG                                                   676
```

( 2 ) INFORMATION FOR SEQ ID NO:42:

( i ) SEQUENCE CHARACTERISTICS:
( A ) LENGTH: 676 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:42:

```
TAAGTAGGCG GTGGAAAATG AACCAAATGG GATTCCTTAA GTAATTGCGA ATGAACAAGG    60
AAATGCTCAG CTTGAAAAAT GGGGCCTTTG GCTTTGAATT GTAATTTTGA AATGTATTGC   120
CAATGGAGGC GCAGGTGCAA GCCTATTGAA AGAAAGCGTC AATGAGGGTG AGATTCCTTT   180
TTGTCATTTG CAGTCCTCCG TGCACGGTAT ATATTTGACG AGTCACACTC CTCGGCATTG   240
GAATGCAAAG TGGGTGGTAA ATTCCATGTA AAGGTAAATA TATTATTGAG ACTGATAGCA   300
AACAAGTACC ATGAGGGAAA TATGAAAAGG ACTTTGAAAA GAGAATTAAA AGAGTCTGCA   360
TTTGCTGAAC AGAAAGCAAA CAGAATTGAT TTTACTTGGT GAGATTGTTG CGCTTACTCT   420
ATCATTTATA TGGTTGATGT GGGTGCGATG GTTCTTACCT TGAATGTCAG CTTCTATTTC   480
TGCAAATCAT TACCCTTGCA CATGAATGGT AAYTTGCCTG CGGGTATTGG AATGCATGTG   540
TTTGCAATGA TTTGTGATTT GACGCATGTG TTTGGTGAAA TTTGTATATG CTCTTTTGTC   600
GAAGGGGAAA GCTTACTTTT TTGAGCATTG CAAGCCCTTA CACATCAGTG CTGGCAAAAT   660
GTTTCTGCTT GACCCG                                                   676
```

( 2 ) INFORMATION FOR SEQ ID NO:43:

( i ) SEQUENCE CHARACTERISTICS:
( A ) LENGTH: 676 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:43:

```
TAAGTAGGCG GTGGAAAATG AACCAAATGG GATTCCTTAA GTAATTGCGA ATGAACAAGG     60
AAATGCTCAG CTTGAAAAAT GGGGCCTTTG GCTTTGAATT GTAATTTTGA AATGTATTGC    120
CAATGGAGGC GCAGGTGCAA GCCTATTGAA AGAAAGCGTC AATGAGGGTG AGATTCCTTT    180
TTGTCATTTG CAGTCCTCCG TGCACGGTAT ATATTTGACG AGTCACACTC CTCGGCATTG    240
GAATGCAAAG TGGGTGGTAA ATTCCATGTA AAGGTAAATA TATTATTGAG ACTGATAGCA    300
AACAAGTACC ATGAGGGAAA TATGAAAAGG ACTTTGAAAA GAGAATTAAA AGAGTCTGCA    360
TTTGCTGAAC AGAAAGCAAA CAGAATTGAT TTTACTTGGT GAGATTGTTG CGCTTACTCT    420
ATCATTTATA TGGTTGATGT GGGTGCGATG GTTCTTACCT TGAATGTCAG CTTCTATTTC    480
TGCAAATCAT TACCCTTGCA CATGAATGGT AATTTGCCTG CGGGTATTGG AATGCATGTG    540
TTTGCAATGA TTTGTGATTT GACGCATGTG TTTGGTGAAA TTTGTATATG CTCTTTTGTC    600
GAAGGGGAAA GCTTACTTTT TTGAGCATTG CAAGCCCTTA CACATCAGTG CTGGCAAAAT    660
GTTTCTGCTT GACCCG                                                    676
```

( 2 ) INFORMATION FOR SEQ ID NO:44:

( i ) SEQUENCE CHARACTERISTICS:
( A ) LENGTH: 661 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:44:

```
TAAGTAGGCG GTGGAAAATA AACCAAATGG GATTCCTTAA GTAATGGCGA ATGAACAAGG     60
AACTGCTCAA CTTGAAAATC GGGGCTTCTG GCCTTGAATT GTAATTTTGA AATGTATTGC    120
CAATGGAGGC GCAGGTGCAA GCCAATTGAA AGAAAGCGTC AAAGAAGGTG AAAATCCTTT    180
TTGTCATTTG CAGCCCTCCG TGCACGGTAT ATATTTGACG AGTCACACTC CTCGGCATTG    240
GAATGCAAAG TGGGTGGTAA ATTTCATGTA AAGATTAATA TATTATTGAG RCTGATAGCG    300
AACAAGTACC ATGAGGGAAA TATGAAAAGG ACTTTGAAAA GAGAATTAAA AGAGTCTGCA    360
CTTGCTGAAC AGAAAGCAAA CAGAAGTGAT TATGCTTGGT AAGATTGTTG CGTCTTGTTG    420
TTCTGCAACT TGGGCGCAGT GGTTCTTACC TTGTCTGCCA GCATCTTTTC TGCAAATCAG    480
AACCCTGGCA CATGACTTGT AAAACGCCTG CGGGTGTTGG AATGCATGTG TTTGCTATGA    540
TTTGTGATTA GATTTGTGCG CGTGGTGCTT CGGTATGTGG CTCTTTGCTG TGGGGGAATT    600
MTCCTCCRCC CTGCTGAATC CCTTGCRCTA CATCGCTGGC AAAATGTTTC TGCTTGACCC    660
G                                                                    661
```

( 2 ) INFORMATION FOR SEQ ID NO:45:

( i ) SEQUENCE CHARACTERISTICS:
( A ) LENGTH: 669 base pairs
( B ) TYPE: nucleic acid
( C ) STRANDEDNESS: single
( D ) TOPOLOGY: linear ( i i ) MOLECULE TYPE: rRNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:45:

```
UAAGUAAGCG GAGGAUAAGA AACUAAAUAG GAUUCCCUCA GUAAUGGCGA AUGAACAGGG    60
AUCAGCUCAG CAUGGAAAUU GGGCCCUCGG CCUUGAAUUG UAGUCUCGAG AUGCAUCGCC   120
AAUGGAGGCG CAGAUGUAAG CCUCUUGGAA AAGAGCAUCA ACGAGGGUGA GAGUCCCGUU   180
UGUCAUCUGC ARUCCCCCAU GCACGGCGUG CUUCUAAGAG UCGCGUUCCU CGGAAUUGGA   240
GCGUCAAUUG GGUGGCAAGC UUCAAAAAAG GGAGUCAUGC AAAUGAGACG CAUCGCUAAC   300
AAGUACCAUG AGGGAAAGGU GAAAAGGACU UUGAAAAGAG AGUUAAAAGU GCCUGAAAUU   360
GCUGAAAGGG AAGCGAAUGG AACCAGUGUU GCUUGGCGAG AGUUGUCGUA CGCACUUCGC   420
GUGUGGUGGU UCUUGCCUUG UGUGUCAUGG CUGGCUGUGU GUGCUAGGUA CAACUCAUAC   480
AUGGACUGUC UCCUGCGCGC AGCCUACAGG AUCGUGGAAA ACGCCAGGGG CAUGGGAGUG   540
UACCGCGUGU CUGGUUGCAG UGCUGCUUGA UCUUGUGCGC UGGGAUGGAG CUCGCUCCUA   600
CAACCUCCCU UCUAAGGUCU CAGCGCUUCC CUGACACAUA GCGAUGACUA AAUGGUUCUA   660
UUCGACCCG                                                          669
```

( 2 ) INFORMATION FOR SEQ ID NO:46:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: preRNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:46:

```
ACCCGCTGAA TTTAAGCATA                                                20
```

( 2 ) INFORMATION FOR SEQ ID NO:47:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO -continued ( i v ) ANTI-SENSE: NO ( v ) FRAGMENT TYPE:

( v i ) ORIGINAL SOURCE:

( x i ) SEQUENCE DESCRIPTION: SEQ ID NO:47:

CCTTGGTCCG TCTTTCAAGA 20

( 2 ) INFORMATION FOR SEQ ID NO:48:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:48:

ACTCTCTTTT CAAAGTCCTT 20

( 2 ) INFORMATION FOR SEQ ID NO:49:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:49:

TGAAAAGGAC TTTGAAAAGA 20